(12) United States Patent
Kellenberger et al.

(10) Patent No.: US 8,173,609 B2
(45) Date of Patent: *May 8, 2012

(54) MACROLIDES USEFUL AGAINST INFLAMMATORY AND ALLERGIC DISEASES

(75) Inventors: Johannes Laurenz Kellenberger, Riehen (CH); Jürg Dreier, Witterswil (CH); Stefan Bernhard Reinelt, Weil Am Rhein (DE)

(73) Assignee: Basilea Pharmaceutica AG, Basel (CH)

( * ) Notice: Subject to any disclaimer, the term of this patent is extended or adjusted under 35 U.S.C. 154(b) by 295 days.

This patent is subject to a terminal disclaimer.

(21) Appl. No.: 12/375,963

(22) PCT Filed: Aug. 8, 2007

(86) PCT No.: PCT/EP2007/058247
§ 371 (c)(1),
(2), (4) Date: Sep. 25, 2009

(87) PCT Pub. No.: WO2008/017696
PCT Pub. Date: Feb. 14, 2008

(65) Prior Publication Data
US 2010/0120706 A1 May 13, 2010

(30) Foreign Application Priority Data
Aug. 9, 2006 (EP) .................................. 06016591

(51) Int. Cl.
*A61K 31/70* (2006.01)
*C07H 17/08* (2006.01)
(52) U.S. Cl. .............................. 514/29; 536/7.3; 536/7.4
(58) Field of Classification Search .................... 536/7.4
See application file for complete search history.

(56) References Cited

U.S. PATENT DOCUMENTS
2004/0038915 A1    2/2004   Vo et al.

FOREIGN PATENT DOCUMENTS
| WO | 0216380 A1 | 2/2002 |
| WO | 03004509 A2 | 1/2003 |
| WO | 03024986 A1 | 3/2003 |
| WO | 03042228 A1 | 5/2003 |
| WO | 03072588 A1 | 9/2003 |
| WO | 2005067919 A1 | 7/2005 |
| WO | 2006084410 A1 | 8/2006 |

OTHER PUBLICATIONS

Culic et al., "Anti-inflammatory Effects of Macrolide Antibiotics," European Journal of Pharmacology, 2001, v. 49, pp. 209-229.
Lipworth, "Phosphodiesterase-4 inhibitor for asthma and chronic obstructive pulmonary disease," The Lancet 2005;365:167-175.
Giembycz, "Life after PDE4: overcoming adverse events with dual-specificity phosphodiesterase inhibitors," Curr Opin Pharmacol 2005; 5: 238.
J. O. Odingo, "Inhibitors of PDE4: a review of recent patent literature," Expert Opinion on Therapeutic Patents, Jul. 2005, vol. 15, No. 7, pp. 773-787.
Hendrix, et al., Methods and Principles in Medicinal Chemistry (2004), vol. 22 (Chemogenomics in Drug Discovery), 243-288 (Wiley-VCH).
Chen et al, "Synthetic studies of erythromycin derivatives: 6-O-methylation of (9S)-12,21-anhydro-9-dihydroerythromycin A derivatives," Tetrahedron, vol. 59, Issue 35, Aug. 25, 2003, pp. 7033-7045.
Tanikawa et al, "Synthesis and Antibacterial Activity of a Novel Series of Acylides: 3-O-(3-Pyridyl)acetylerythromycin A Derivatives," J. Med. Chem., 2003, 46 (13), pp. 2706-2715.
Labro, "Anti-inflammatory activity of macrolides: a new therapeutic potential?" Journal of Antimicrobial Chemotherapy, 1998, 41, Suppl. pp. 37-46.
Baker et al, "Modification of macrolide antibiotics. Synthesis of 11-deoxy-11-(carboxyamino)-6-O-methylerythromycin A 11,12-(cyclic esters) via an intramolecular Michael reaction of O-carbamates with an .alpha.,.beta.-unsaturated ketone," J. Org. Chem., 1988, 53 (10), pp. 2340-2345.
Kashimura et al., "Synthesis and antibacterial activity of the tricyclic ketolides : TE-802 and its analogs," J. Antibiotics, 2001, 54, pp. 664-678.
Ellervik, et al., "Guanidine/Guanidinium Nitrate; a Mild and Selective O-Deacetylation Reagent that leaves the N-Troc Group Intact," Tetrahedron Letters 1997, 38(9), pp. 1627-1628.
Yu et al., "Substituted Pyrazolopyridines as Potent and Selective PDE5 Inhibitors: Potential Agents for Treatment of Erectile Dysfunction," J. Med. Chem., 2001, 44 (7), pp. 1025-1027. Also, supporting information for this article is enclosed.
Torphy et al., "Stimulation of beta adrenoceptors in a human monocyte cell line (U937) up-regulates cyclic AMP-specific phosphodiesterase activity," J. Pharmacol Exp. Ther. Dec. 1992; 263(3):1195-1205.
The International Search Report and Written Opinion by the International Searching Authority, issued on Sep. 20, 2007, in the PCT application No. PCT/EP2007/058247.

(Continued)

*Primary Examiner* — Elli Peselev

(57) ABSTRACT

New macrolide general compounds of formula I

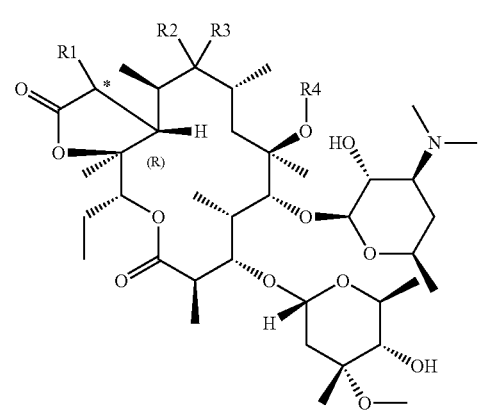

with improved activity making them useful for inhibiting human phosphodiesterase 4 and treating chronic obstructive pulmonary disease (COPD).

15 Claims, No Drawings

MACROLIDES USEFUL AGAINST INFLAMMATORY AND ALLERGIC DISEASES

This application is a National Stage Application of PCT/EP2007/058247 filed Aug. 8, 2007, which claims priority from European Patent Application 06016591.7 filed on Aug. 9, 2006. The priority of both said PCT and European Patent Application is claimed.

The invention relates to novel macrolide compounds, the use of said compounds as medicaments, in particular for the treatment or prevention of inflammatory and allergic diseases, pharmaceutical compositions containing said compounds and to processes for their preparation. The invention relates in particular to macrolide compounds with anti-inflammatory activity mediated primarily through inhibition of phosphodiesterase 4 (PDE4) which makes them useful for the treatment and/or prevention of inflammatory and allergic diseases such as chronic obstructive pulmonary disease (COPD), asthma, rheumatoid arthritis, atopic dermatitis or inflammatory bowel disease.

Cyclic adenosine monophosphate (cAMP) is a key second messenger in cells. Increased levels of cyclic AMP are known to suppress cellular responses in various types of inflammatory and immune cells including lymphocytes, monocytes, macrophages, neutrophils, eosinophils, basophils and lung epithelial cells. Intracellular concentrations of cAMP are regulated by adenylyl cyclase and by cyclic nucleotide phosphodiesterases (PDEs). PDEs are a family of enzymes that inactivate cyclic nucleotides cAMP and cGMP through hydrolysis to AMP and GMP. The cAMP-specific enzyme PDE4 is the predominant enzyme in pro-inflammatory cells. PDE4 has been shown to be involved in inflammatory processes (cf. e.g. Lipworth B. J., Lancet (2005) 365, p. 167 or Giembycz M. A., Curr. Opin. Pharmacol. (2005), 5, p. 238). Therefore, inhibitors of PDE4 are believed to be useful in the treatment and/or prophylaxis of inflammatory and allergic diseases such as asthma, chronic bronchitis, emphysema, atopic dermatitis, urticaria allergic rhinitis, allergic conjunctivitis, psoriasis, rheumatoid arthritis, chronic obstructive pulmonary disease (COPD), septic shock, ulcerative colitis, Crohn's disease, adult respiratory distress syndrome and multiple sclerosis.

Numerous PDE4 inhibitors have been disclosed in the literature. (see for example J. O. Odingo, Expert. Opin. Ther. Patents, 2005, 15(7), 773; M. Hendrix, C. Kallus, Methods and Principles in Medicinal Chemistry (2004), Vol. 22 (Chemogenomics in Drug Discovery), 243-288 (Wiley-VCH)). Many of the known PDE4 inhibitors show dose-limiting side-effects such emesis and headache.

Erythromycin derivatives having a five-membered lactone ring fused to the 11,12-positions of the macrolactone ring have been disclosed in e.g. WO 02/16380, WO 03/004509, WO 03/042228, WO 03/072588, WO 03/024986, US 2004/0038915 and in WO2005067919. Documents WO 02/16380, WO 03/072588, WO 03/024986 and US 2004/0038915 describe exclusively so-called ketolides having a carbonyl group at position 3 of the erythromycin scaffold. WO 03/042228, WO 03/004509 and WO2005067919 disclose macrolide derivatives with a 11,12 lactone ring and having a cladinose sugar substituent at position 3 of the erythromycin scaffold. These derivatives are however different in structure from those of the invention disclosed hereinafter.

Reduction of the carbonyl group in position 9 of the erythromycin scaffold has also been described, for example in Tetrahedron, 2003, 59, p. 7033 or J. Med. Chem. 2003, 46, p. 2706.

All macrolide compounds described in the above-mentioned documents have been disclosed as useful for the treatment of bacterial infections. Erythromycin-derived macrolides have also been reported to possess anti-inflammatory activity (e.g. Journal of Antimicrobial Chemotherapy, 1998, 41, Suppl. B, 37-46). Furthermore, erythromycin-derived macrolides are known to accumulate in inflammatory cells.

Surprisingly, it has now been found that certain macrolide compounds having a five-membered lactone ring fused to the erythromycin scaffold selectively inhibit PDE4, a newly found activity not described so far for this kind of molecules. These macrolides are therefore useful for the treatment and/or prevention of inflammatory and allergic diseases. The molecules described herein are structurally distinct to currently known PDE4 inhibitors and therefore have the potential to overcome the above-mentioned side effects.

The present invention accordingly relates to macrolide compounds of formula I:

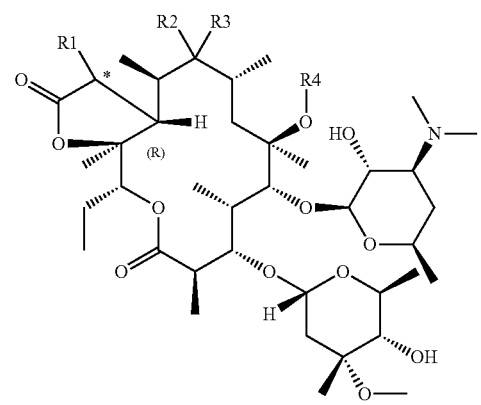

wherein
R1 is a residue —Y—X-Q;
Y is S, SO or $SO_2$;
X is a bond or a linear group consisting of hydrogen atoms and with up to 9 atoms selected from C, N, O and/or S, of which up to 2 atoms can be N and one atom can be O or S, one carbon atom can appear as a CO group and the sulphur atom can appear as an $SO_2$ group and two adjacent C atoms can be present as —CH═CH— or —C≡C— and which group X is unsubstituted or is substituted with —COO—W or —CONH—W;
Q is a residue —V-A1-L-A2-W or, if X does not represent a bond, may also be —NR6R7;
V is a divalent aromatic or heterocyclic group;
W is aryl or heterocyclyl; or in a group —V-A1-L-A2-W, wherein at least one of the groups A1, L or A2 is present, can also be a monovalent substituted or unsubstituted, saturated or unsaturated linear group with up to 5 atoms consisting of C, N, O and/or S of which one carbon can appear as a CO group one sulphur atom can appear as an $SO_2$ group,
A1, A2 are independently of each other either absent or a $C_1$-$C_4$alkylene group;
L is —O—, —S—, —$SO_2$—, —NH—, —CO—, —(CO)O—, —O(OC)—, —(CO)NH—, —NH(CO)—, —($SO_2$)NH—, —HN($SO_2$)—, —HN(CO)NH—, —O(CO)NH—, —NH(CO)O—, or can also be absent if A1 and/or A2 are present;
R2 is hydrogen and
R3 is OR4 or R2, R3 taken together form a C=O group;
R4 is, independently at each occurrence in formula I, hydrogen or an saturated or unsaturated aliphatic group with 1 to 6 carbon atoms;
R6, R7 are independently selected from aryl; aralkyl; heterocyclyl and heterocyclylalkyl; and one of R6 and R7 can also be a group -L-W; and
* indicates a chiral centre which is in the (R) or (S) form;
except for the compound of formula I, wherein
R2, R3 taken together form a C=O group
R4 is methyl and
R1 is

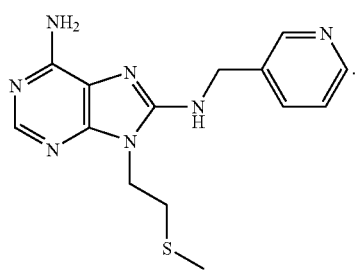

For the purposes of the present invention the term macrolide compounds is understood to include the separate stereomeric forms of the compounds as well as diastereomeric mixtures.

Furthermore, the term macrolide compounds is understood in the present invention to include pharmaceutically acceptable salts and N-oxides of compounds of formula (I), as well as in vivo cleavable esters.

The compounds of the invention exhibit substantial inhibitory activity towards human phosphodiesterases (PDEs), in particular towards PDE4, which has been shown to be involved in inflammatory processes (cf. e.g. Lipworth B. J., Lancet (2005) 365, p. 167 or Giembycz M. A., Curr. Opin. Pharmacol. (2005), 5, p. 238). This is shown in the examples. The use of the compounds according to the present invention for the treatment of diseases and disorders in humans which can be ameliorated or relieved by inhibition of human phodiesterases, in particular phosphodiesterase 4 is therefore a further aspect of the present invention. Based on this activity the present compounds are particularly useful for the prevention and/or treatment of inflammatory diseases as well as for the treatment and/or prevention of allergic diseases.

Important examples of such diseases are chronic obstructive pulmonary disease (COPD), asthma, rheumatoid arthritis, atopic dermatitis or inflammatory bowel disease.

For the purposes of the present invention the terms "aromatic group" and "aryl" refer to aromatic groups with one or more preferably 6-membered nuclei and having from 6 to 14 carbon atoms. Examples are in particular phenyl, naphthyl, anthryl and phenanthryl. These groups may be further substituted with 1, 2, 3 or 4 substituents selected from, for example, alkyl such as defined hereinafter, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyloxy, halogen such as defined hereinafter, halogen substituted alkyl groups such as difluoromethyl or trifluoromethyl, trichloroethyl, cyano, nitro, amino, alkylamino, dialkylamino, alkylthio, mercapto, hydroxy, carbamoyl, carboxyl, an oxo group. In case more than one substituent is attached to the aryl group, these substituents can be identical or different from each other. Also encompassed by the scope of the present invention are different possible regioisomers of a specific group, for example "dimethoxy-phenyl" means that both methoxy substituents may be attached to the phenyl ring in the 2,3-position, the 2,4-position, the 2,5-position, the 2,6-position, the 3,4-position, the 3,5-position and the 3,6-position.

As used herein the term "heterocyclic group" or "heterocyclyl" refers to an unsaturated or saturated, unsubstituted or substituted 5- to 10-membered (mono- or bicyclic) heterocyclic ring system containing at least one hetero atom selected from the group consisting of sulfur, oxygen, and/or preferably nitrogen. Exemplary heterocyclic substituents include, but are not limited to, for example, the following groups: piperidinyl, morpholinyl, 2-, 3- or 4-pyridyl, pyrrolidinyl, piperazinyl, 1H-pyrazol-1-yl, 1H-imidazol-1-yl, 1H-imidazol-2-yl, pyrazinyl, pyrimidyl, pyridazinyl, pyrazolyl, triazinyl, thiazolyl, thiadiazolyl, oxadiazolyl, triazolyl, e.g. 1H[1,2,4]-triazol-1-yl, 1H-tetrazolyl, 2H-tetrazolyl; thienyl, furyl (2-furanyl or 3-furanyl), 1H-azepinyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, tetrahydrothienyl, and the like, or condensed heterocyclic ring systems such as quinolinyl, e.g. quinolin-8-yl, quinolin-5-yl, quinolin-2-yl, quinolin-6-yl, quinolin-3-yl, isoquinolinyl (6-isoquinolinyl), quinazolinyl, 1H-benztriazolyl, 1H-imidazo[4,5-c]pyridinyl, 5H-imidazo[4,5-c]pyridinyl, 1H-imidazo[4,5-b]pyridin-1-yl, 3H-imidazo[4,5-b]pyridin-3-yl, 1H-pyrazolo[3,4-b]pyridinyl, 1,2,3,4-tetrahydro-quinolinyl, 1,2,3,4-tetrahydro-isoquinolinyl, thieno[2,3-b]pyridinyl, benzothiazolyl (e.g. 2-benzothiazolyl), 1H-benzoimidazolyl, 1H-indolyl, 1,2,3,4-tetrahydroquinolinyl, purinyl, e.g. 9H-purin-9-yl, 6-amino-9H-purin-9-yl, 2,6-diamino-9H-purin-9-yl, 1H-purin-6-yl, 1H-2,3-dihydroindol-1-yl, 2,1,3-benzoxadiazol-5-yl, 2,1,3-benzoxadiazol-4-yl, 1,3-benzodioxol-5-yl, 2,3-benzoxazolinyl, 1,2-dihydro-oxazolo[5,4-c]pyridinyl, 6-quinoxalinyl, 2-benzo[b]thien-3-yl, 3,4-dihydro-1H-2-oxo-quinolin-6-yl.

The heterocyclyl groups may be further substituted by one or more substituents. Such substituents include, for example, alkyl groups such as defined hereinafter, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyoxy, halogen such as defined hereinafter, halogen substituted alkyl groups such as trifluoromethyl, trichloroethyl, nitro, amino, alkylamino, dialkylamino, alkylthio, mercapto, hydroxy, carbamoyl, carboxyl, an oxo group. In case more than one substituent is attached to the heterocyclyl group, these substituents can be identical or different from each other. Different regioisomers are also included within the scope of the present definition, for example "dimethylpyridyl" means that both methyl substituents may be attached to the pyridyl at all chemically possible positions. For example both methyl substituents may be attached to the 2-pyridyl in the 3,4-position, the 4,5-position, the 5,6-position, the 3,5-position, the 3,6-position, the and the 4,6-position. Both methyl substituents may be attached to the 3-pyridyl in the 2,4-position, the 2,5-position, the 2,6-position, the 4,5-position, the 4,6-position, the and the 5,6-position. Both methyl substituents may be attached to the 4-pyridyl in the 2,3-position, the 2,5-position, the 2,6-position, and the 3,5-position.

Especially preferred substituents for the heterocyclyl groups are alkyl, alkoxy, oxo, halogen, amino, alkylamino or dialkylamino, wherein alkyl and alkoxy are as defined hereinabove.

Examples of preferred substituted heterocyclic rings are 1H-pyrimidin-2,4-dione, 1H,3H-pyrimidin-2,4-dione-5-methyl, 1H-pyrimidin-4-amino-2-on, 6-amino-9H-purin, 6-dimethylamino-9H-purin, 2,6-diamino-9H-purin, 6-amino-8-[(3-pyridinylmethyl)amino]-9H-purin, 4-amino-imidazo[4,5-c]pyridine, 4-methoxy-imidazo[4,5-c]pyridine, 1-ethyl-pyrazolo[3,4-b]pyridine, 4-phenyl-1H-pyrazol, 3-(pyridin-3-yl)-1H-pyrazol, 3-(pyridin-4-yl)-1H-pyrazol-1-yl, 3-(pyridin-3-yl)-1H-imidazol-1-yl, 3-(pyridin-4-yl)-1H-imidazol-1-yl, 3-(pyridin-3-yl)-1H-[1,2,4]-triazol, 3-(pyridin-4-yl)-1H-[1,2,4]-triazol and 2-oxo-1,2,3,4-tetrahydroquinoline.

As used herein the term "alkyl" refers to branched or preferably straight chain saturated hydrocarbon groups having preferably 1 to 6 carbon atoms. Such groups are for example methyl, ethyl, n-propyl, isopropyl, tertiary butyl, pentyl, hexyl, and the like. Such alkyl groups may be further substituted with one or more substituents selected from, for example, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyloxy, halogen such as defined below, halogen substituted alkyl groups such as difluoromethyl or trifluoromethyl, trichloroethyl, cyano, nitro, amino, alkylamino, dialkylamino, alkylthio, mercapto, hydroxy, carbamoyl, carboxyl, or oxo. More than one substituent can be either identical or different from each other.

The term aliphatic group refers to branched or preferably straight chain saturated hydrocarbon groups having preferably 1 to 6 carbon atoms, which can be saturated or unsaturated. Examples include those mentioned for alkyl, vinyl, n-propenyl, n-propinyl, butenyl groups, butadienyl, pentenyl groups, and the like.

The term "halogen" refers to fluorine, chlorine, bromine or iodine.

In the combinations "heterocyclylalkyl" and "aralkyl" the single parts "heterocyclyl", "ar" (aryl) and "alkyl" have the meanings indicated above.

The term $C_1$-$C_4$alkylene group refers e.g. to methylene, ethylene, n-propylene and n-butylene.

R1 is a residue of formula —Y—X-Q.

In this formula Y may generally be S, SO or $SO_2$; preferred are S and $SO_2$, in particular S.

X is either a bond; i.e. is "absent", or a linear group consisting of hydrogen atoms and up to 9 atoms selected from C, N, O and/or S, of which up to 2 atoms can be N and one atom can be O or S, one carbon atom can appear as a CO group and the sulphur atom can appear as an $SO_2$ group. Two adjacent C atoms can also be present as —CH=CH— or —C≡C—. The group X can be unsubstituted or is substituted with a substituent of formula —COO—W or —CONH—W, wherein W has the meaning defined herein. As already indicated the spacer group X with up to 9 atoms may carry additional hydrogen atoms to saturate a C atom to form a methylene group or to saturate a N atom to form an amino group. Preferably, this spacer consists of 2 to 5 atoms selected from C, N, O and/or S.

Preferred groups X are:
$(CH_2)_n$, $(CH_2)_mOCH_2$, $(CH_2)_2NCH_3(CH_2)_2$, $CH_2CH_2NH$, $(CH_2)_pCOO$, $(CH_2)_pCONH$ or $HN(CH_2)_p$, where n and p are 1-3 and m is 0 or preferably 1-3.

Particularly preferred groups X are ethyl and propyl.

Suitable combinations of Y and X are e.g as follows:

For Y=S, X is ethyl, propyl, $CH_2CO$, $CH_2COCH_2$, $CH_2CONR$, $CH_2CONRCH_2$, $CH_2CONRCH_2CH_2$, $CH_2CH_2CONR$, $CH_2CH_2CONRCH_2$, $CH_2CH_2NR$, $CH_2CH_2NRCO$, $CH_2CH_2NRSO_2$, $CH_2CH_2NRCOO$, $CH_2CH_2OCH_2$, $CH_2SO_2NR$, $CH_2SO_2NRCH_2$, $CH_2CH_2OCONR$, $CH_2CH=CH$ or $CH_2C≡C$; where R in the above expressions is hydrogen or methyl.

In formula I Q is a residue of the formula either —V-A1-L-A2-W. In the alternative and if X does not represent a bond, Q in formula I may also be —NR6R7.

V can be a divalent aromatic or heterocyclic group, e.g. one of those specifically mentioned above.

In another preferred group of compounds of formula I V is a divalent group of formula

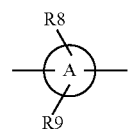

wherein

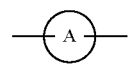

is a phenylene ring or a x-membered saturated or unsaturated divalent heterocycloaliphatic or heteroaromatic ring containing from 2 to (x-1) carbon atoms with x being 5 to 8, preferably 5 or 6, and from 1 to 3 hetero atoms selected from the group consisting of sulfur, and preferably oxygen and nitrogen, R8 and R9 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, cyano, nitro, amino, $C_1$-$C_4$alkylamino, di($C_1$-C4)alkylamino, $C_1$-$C_4$alkylthio, mercapto, hydroxy, carbamoyl, a carboxyl group, an oxo group; or aryl or heterocyclyl, which may be unsubstituted or substituted with one or more of the above identified substituents other than aryl or heterocyclyl, or when both substituents R8 and R9 are located at adjacent carbon atoms of the ring

these two substituents can be taken together with said adjacent carbon atoms to form a 5- or 6-membered aromatic or a x-membered saturated or unsaturated heterocycloaliphatic or heteroaromatic ring containing from 2 to (x-1) carbon atoms with x being 5 to 8, preferably 5 or 6, and from 1 to 3 hetero atoms selected from the group consisting of sulfur and preferably, oxygen and nitrogen, wherein V can have all together one to four substituents of the kind as defined for R8 and R9 and the free valences can be located either on one or on both rings of the group V.

Particularly preferred meanings of V include:

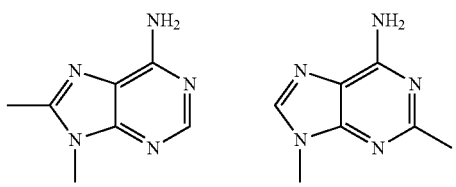

-continued

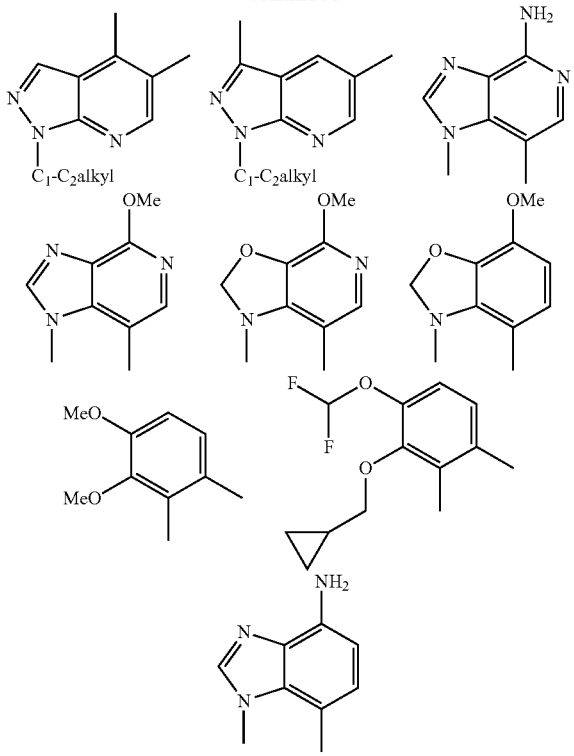

W in formula I can be either aryl or heterocyclyl as explained above.

In a group —V-A1-L-A2-W, wherein at least one of the groups A1; L or A2 is present, W can also be a monovalent substituted or unsubstituted, saturated or unsaturated linear group with up to 5 atoms consisting of C, N, O and/or S of which one carbon can be appear as a CO group one sulphur atom can appear as an $SO_2$ group. In this case W may also carry additional hydrogen atoms to saturate a C or a N atom, as already described above with reference to group X.

In a preferred embodiment of formula I W represents a group of formula

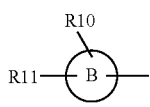

wherein

is a phenyl ring or a x-membered saturated or unsaturated heterocycloaliphatic or heteroaromatic ring containing from 2 to (x-1) carbon atoms with x being 5 to 8, preferably 5 or 6, and from 1 to 3 hetero atoms selected from the group consisting of sulfur, and preferably oxygen and nitrogen, R10 and R11 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, cyano, nitro, amino, $C_1$-$C_4$alkylamino, di($C_1$-$C_4$)alkylamino, $C_1$-$C_4$alkylthio, mercapto, hydroxy, carbamoyl, a carboxyl group, and an oxo group; or when both substituents R10 and R11 are located at adjacent carbon atoms of the ring

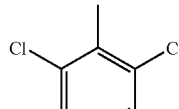

these two substituents can be taken together with said adjacent carbon atoms to form a 5- or 6-membered aromatic or a x-membered saturated or unsaturated heterocycloaliphatic or heteroaromatic ring containing from 2 to (x-1) carbon atoms with x being 5 to 8, preferably 5 or 6, and from 1 to 3 hetero atoms selected from the group consisting of sulfur and preferably, oxygen and nitrogen, wherein W can have all together one to four substituents of the kind as defined for R10 and R11 and the free valence can be located on either ring of the group W.

Particularly preferred examples of W are the following groups:

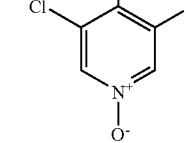

Other specific examples of W include

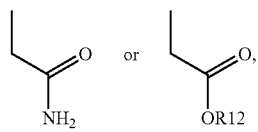

wherein R12 is hydrogen or $C_1$-$C_4$alkyl, in particular methyl.

In a group —V-A1-L-A2-W groups A1 and A2 are, in general, independently of each other either absent or a $C_1$-$C_4$alkylene group. L is generally selected from —O—, —S—, —$SO_2$—, —NH—, —CO—, —(CO)O—, —O(OC)—, —(CO)NH—, —NH(CO)—, —($SO_2$)NH—, —HN($SO_2$)—, —HN(CO)NH—, —O(CO)NH—, and —NH(CO)O— in such group, but may also be absent if A1 and/or A2 are present.

In preferred examples of macrolide compounds according to the invention A1 and A2 are independently of each other either absent or represent a $C_1$-$C_2$alkylene group; and L is selected from —NH—, —(CO)NH— and —NH(CO)—; or is absent.

Particularly preferred are the compounds of formula (I) wherein

A1, A2 are independently of each other either absent or a C$_1$-C$_2$alkylene group;

L is —NH—, —(CO)NH— or —NH(CO)—;

V is a divalent group of formula

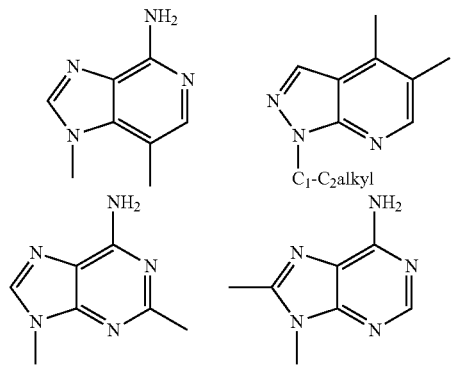

and

W is a group of formula

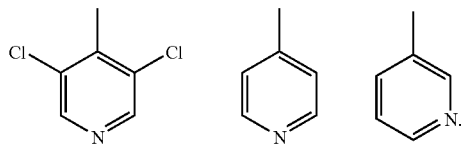

Also preferred are the compounds according to the present invention, in particular those mentioned in the preceeding paragraph, wherein Y is —S— and X is —CH$_2$—CH$_2$—CH$_2$— or, preferably, —CH$_2$—CH$_2$—NH— linked to the residue Q via the NH group or —CH$_2$—CH$_2$—, most preferably —CH$_2$—CH$_2$—.

If X does not represent a bond in formula I, then Q may also be —NR6R7. In this case R6, R7 may be independently selected from aryl, aralkyl, heterocyclyl and heterocyclylalkyl, e.g. as explained above, and one of R6 and R7 can also be a group -L-W; wherein L and W have one of the meanings mentioned above.

Preferred examples of corresponding macrolide compounds according to the invention are compounds of formula I wherein Q is a group —NR6R7 and has one of the following formulae

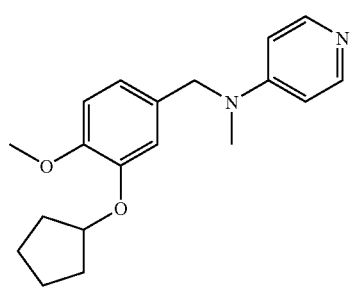

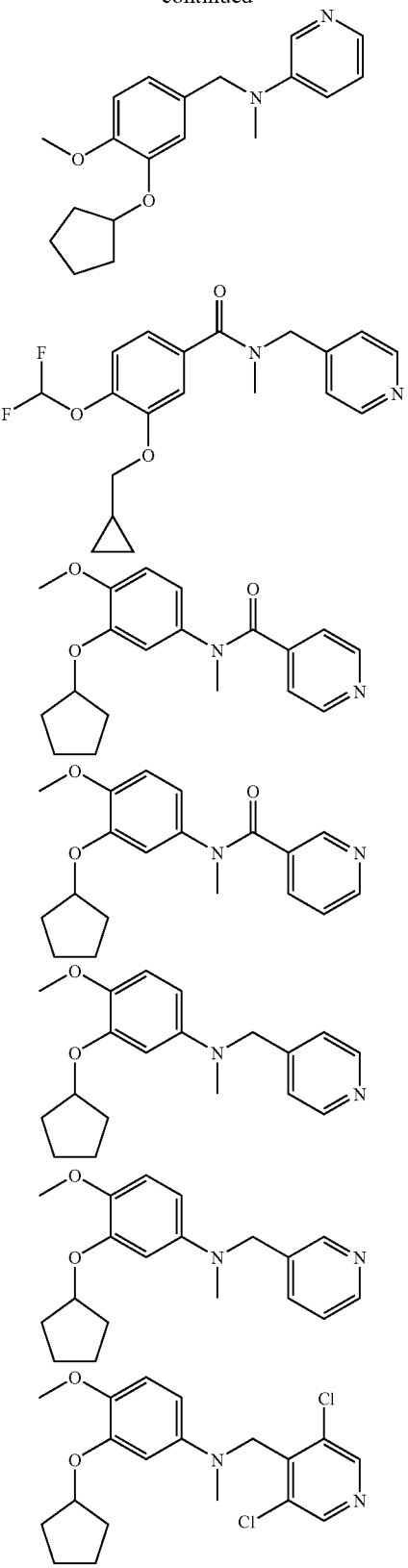

It is furthermore preferred if R2 in formula I represents a hydrogen atom, in particular if R3 is simultaneously hydroxyl or vinyloxy.

Preferred as well are compounds of formula I wherein R2 and R3, taken together, form a C═O group.
Also preferred are compounds according to the invention wherein R4 in formula I is either hydrogen or, more preferably, methyl.
Some specific examples of compounds according to the invention are the following compounds:
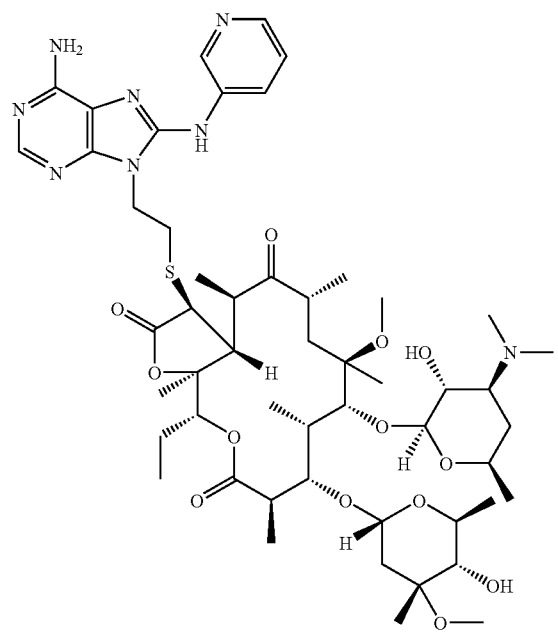
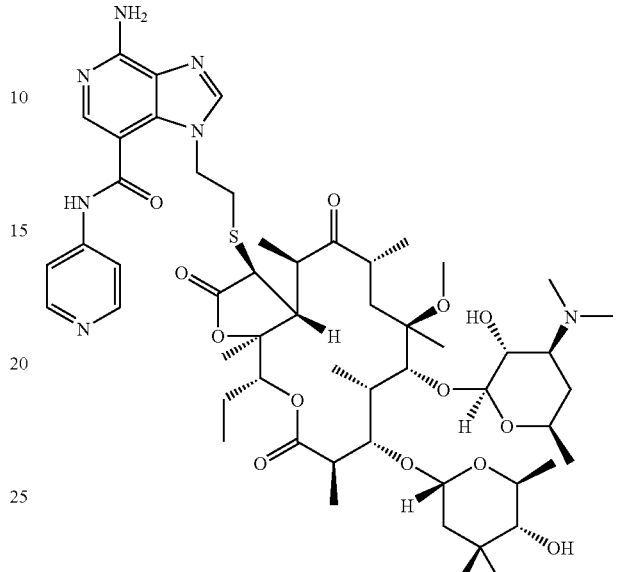
-continued
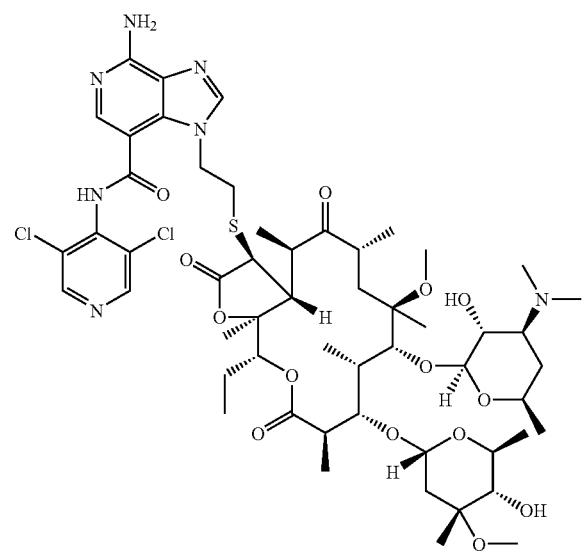
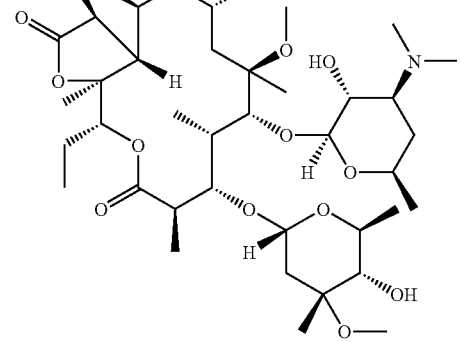

-continued
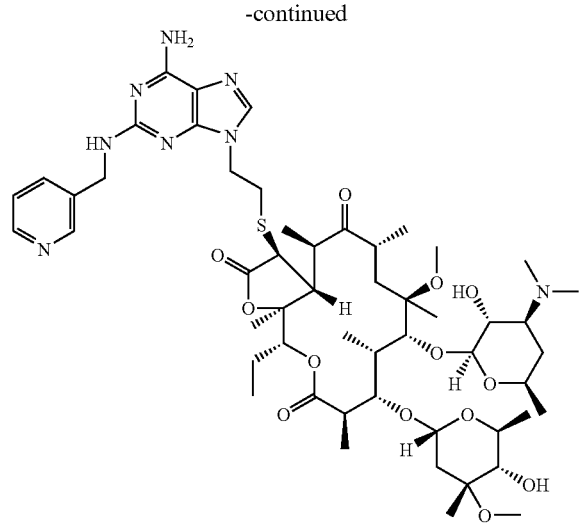
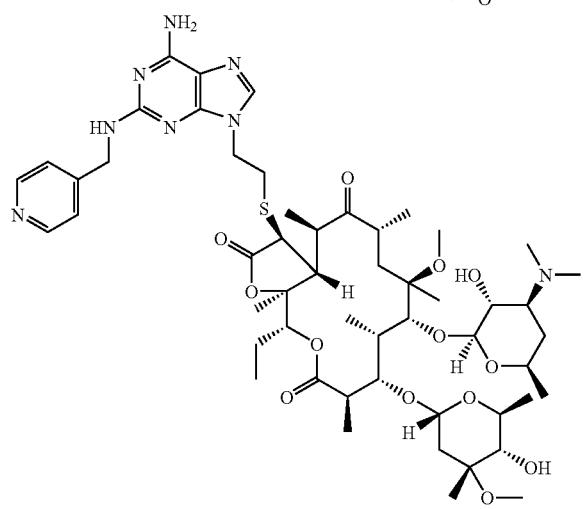
as well as the compound of formula
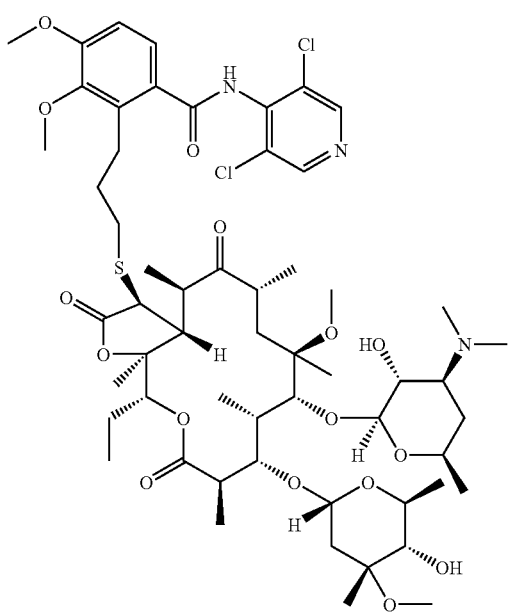
and the compounds of formula
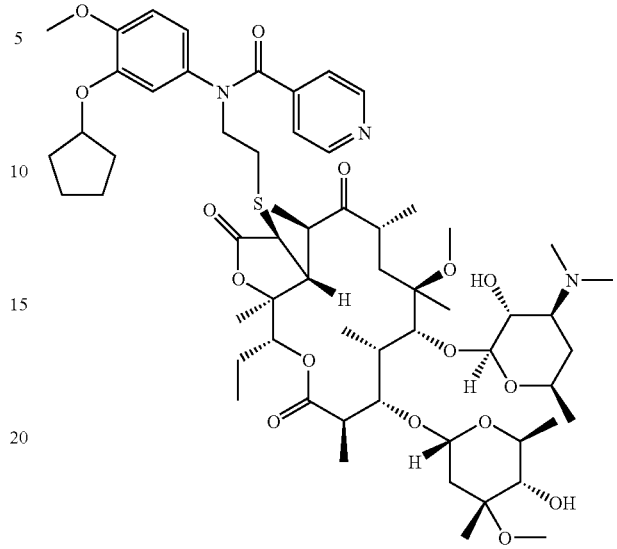
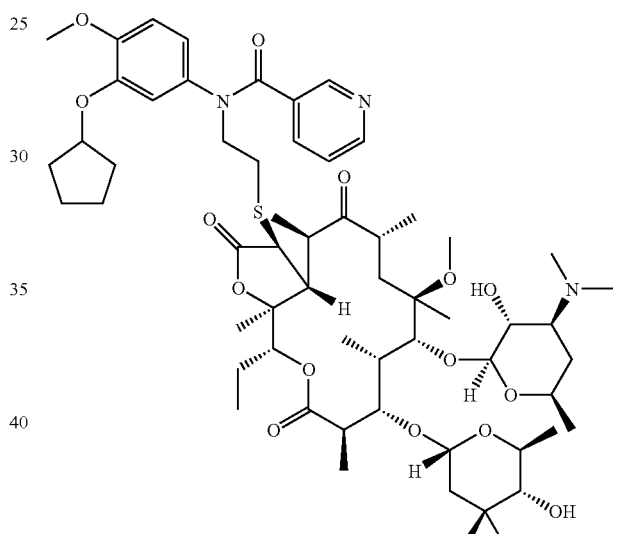
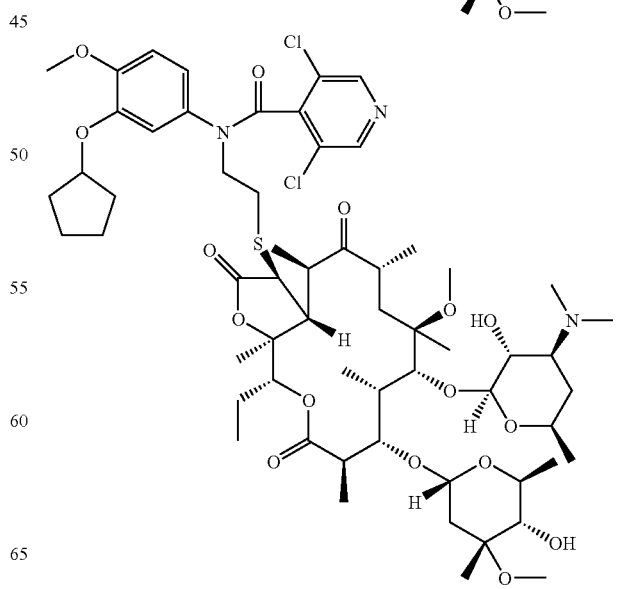

-continued
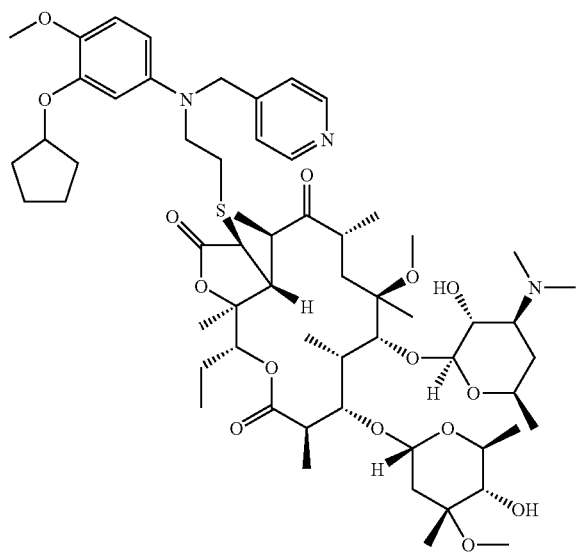
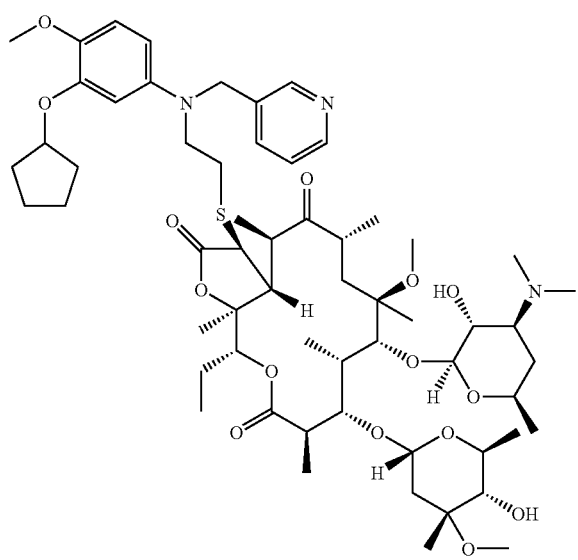
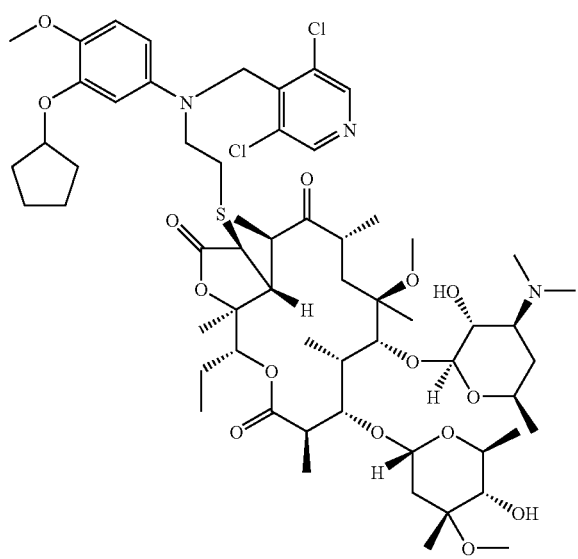
The most preferred compounds are the following:
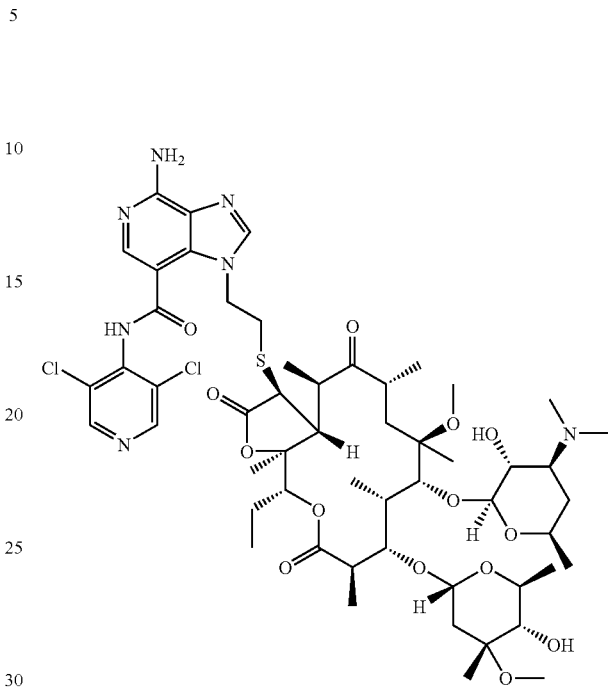
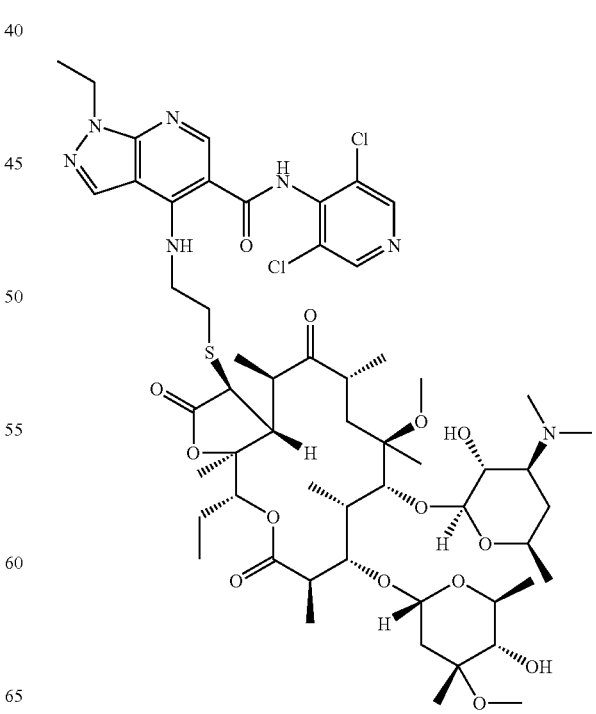

-continued

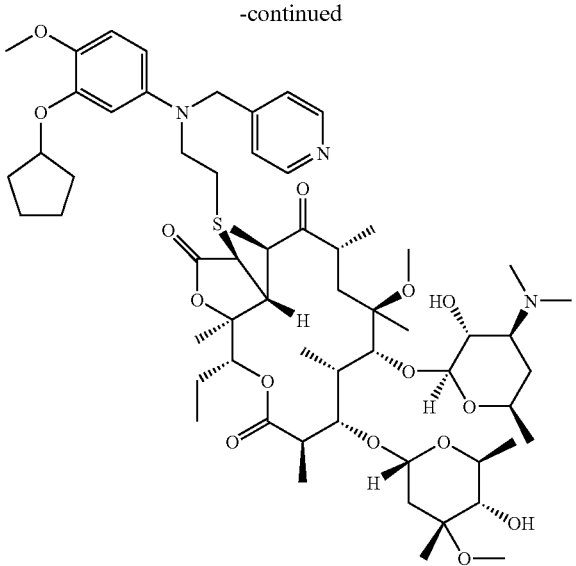

As already indicated above, the macrolide compounds of formula I can, if desired, also be present and used as pharmaceutically acceptable acid addition salts. Not only salts with inorganic acids, but also salts with organic acids come into consideration. Hydrochlorides, hydrobromides, sulfates, nitrates, citrates, acetates, trifluoroacetates, maleates, succinates, methanesulphonates, p-toluenesulphonates and the like are examples of such salts.

Further, the compounds of formula I can be in form of in vivo cleavable esters, for example esters with of the 2'-hydroxy group of the sugar moiety. Suitable esters are generally acetates, pivaloyl esters, tartrates, maleates, succinates, and the like.

The compounds of the present invention including their pharmaceutically acceptable acid addition salts or in vivo cleavable esters thereof are useful for the prevention and/or treatment of diseases such as chronic obstructive pulmonary disease (COPD), asthma, rheumatoid arthritis, atopic dermatitis or inflammatory bowel disease.

The compounds of the present invention and their pharmaceutically acceptable acid addition salts or in vivo cleavable esters thereof can also be used for the prevention and/or treatment of diseases such as chronic bronchitis, emphysema, urticaria, allergic rhinitis, allergic conjunctivitis, psoriasis, septic shock, adult respiratory distress syndrome and multiple sclerosis.

The compounds in accordance with the invention can be used as medicaments. They possess good oral absorption properties. A further embodiment of the present invention are thus medicaments comprising compounds of formula I, their pharmaceutically acceptable acid addition salts, N-oxides or in vivo cleavable esters thereof for the treatment and prevention of infectious diseases, for example, in the form of pharmaceutical preparations for enteral (oral) administration. The products in accordance with the invention can be administered, for example, perorally, such as in the form of tablets, film coated tablets, sugar coated tablets, hard and soft capsules, solutions, emulsions or suspensions, or rectally, such as in the form of suppositories, or parenterally e.g. by injection, or nasally, or by inhalation or transdermally, or locally for example by topical administration, preferably the compounds are administered topically or orally.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

It is contemplated that the compounds are ultimately embodied into compositions of suitable oral, parenteral or topical dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as microcrystalline cellulose, calcium phosphate or lactose; disintegrating agents, such as starch, crosslinked carboxymethylcellulose sodium or crosslinked polyvinylpyrrolidone; and lubricating agents, such as talc, magnesium stearate, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, film coated tablets, sugar coated tablets and hard capsules there can be used, for example, lactose, maize starch or derivatives thereof, talc, stearic acid or its salts. Suitable carriers for soft capsules are, for example, vegetable oils, waxes, fats and semi-solid and liquid polyols (depending on the nature of the active substance). Suitable carrier materials for the preparation of solutions and syrups are, for example, water, alcohols, polyols, saccharose, invert sugar and glucose. Suitable carrier materials for suppositories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavoring agents, salts for adjusting the osmotic pressure, buffers, coating agents and antioxidants.

The compounds of formula I and their acid addition salts, N-oxides or in vivo cleavable esters thereof can be used for parenteral administration and for this purpose are preferably made into preparations for injection as lyophilisates or dry powders for dilution with customary agents, such as water or isotonic common salt solution.

The compounds of formula I and their acid addition salts, N-oxides or in vivo cleavable esters thereof can be used for topical administration and for this purpose are preferably made into preparations as ointments, creams or gels.

For the treatment and/or prevention of inflammatory and allergic diseases in mammals, humans and non-humans, a daily dosage of about 10 mg to about 2000 mg, especially about 50 mg to about 1000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 10 mg, 100 mg, 250 mg, 500 mg and 1000 mg can be contemplated.

The preparation of compounds of formula I is carried out according to schemes 1-5.

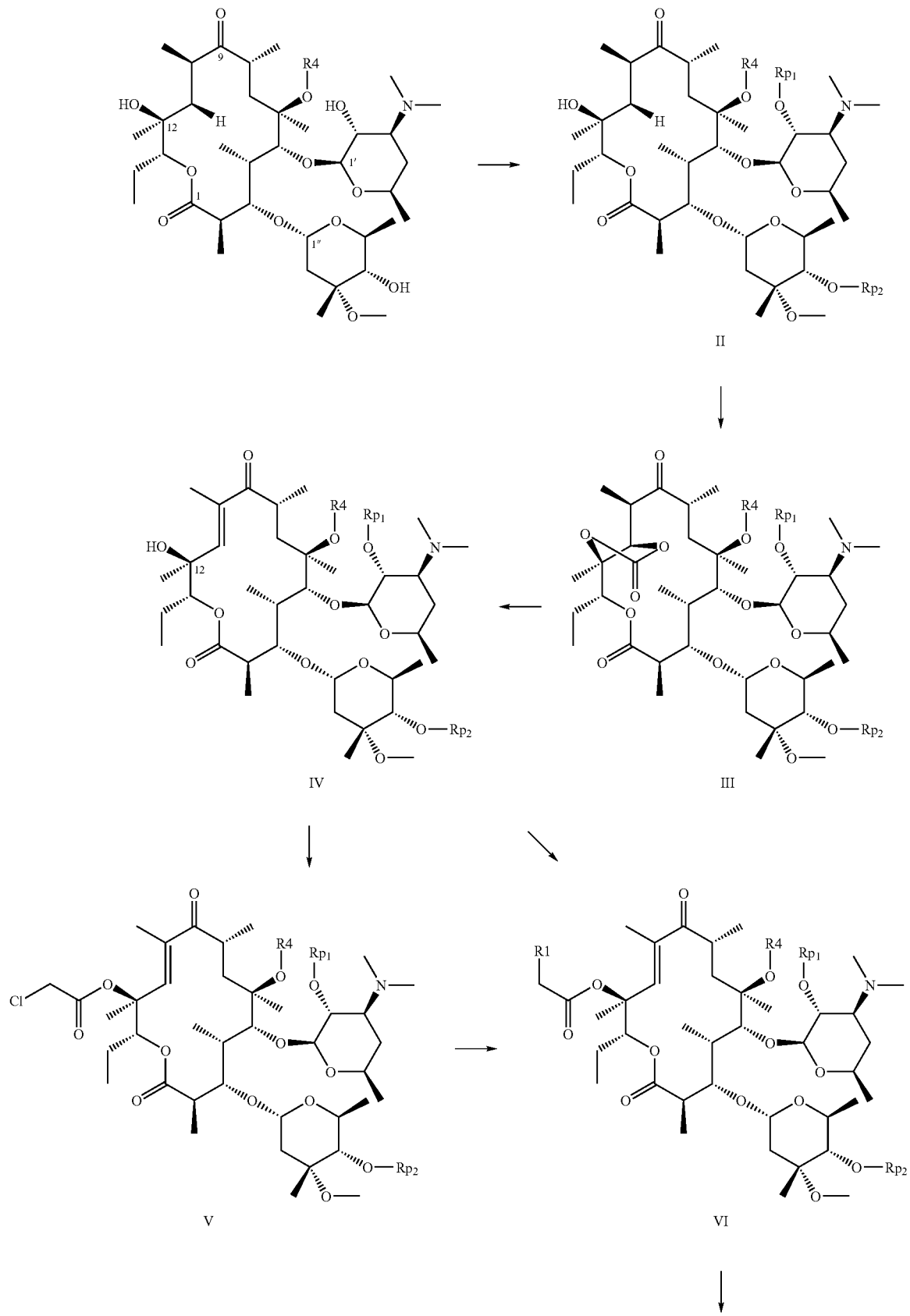
Scheme 1

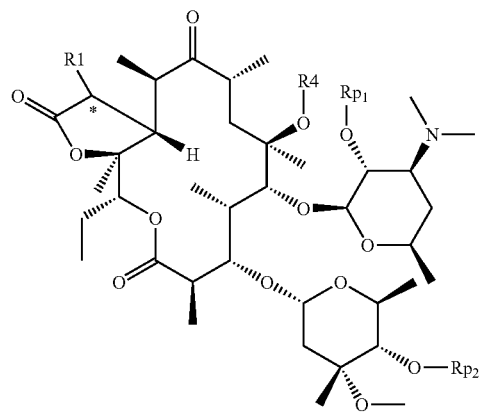

VII

Compounds of the present invention can be prepared starting from erythromycin A, clarithromycin, or any other 6-O-alkyl-erythromycin A, 6-O-alkenyl-erythromycin A or 6-O-alkynyl-erythromycin A. The preparation of compounds of formula II, III and IV wherein $Rp_1$ and $Rp_2$ are H, acetyl, benzoyl or any other suitable hydroxyl protecting group can be prepared by methods well known in the art (scheme 1). To obtain compounds of formula II wherein $Rp_1$ and $Rp_2$ are as defined above the 2'- and 4"-hydroxyl groups of starting macrolide can be protected either sequentially or simultaneously by reaction with a suitable acid anhydride or acid chloride as described in, for example, Baker et al., J. Org. Chem. 1988, 53, 2340-2345 and Kashimura et al., J. Antibiotics, 2001, 54, 664-678. Compounds of formula II can then for example be transformed into compounds of formula IV in a similar way as described in Baker et al., J. Org. Chem. 1988, 53, 2340-2345.

The hydroxy group at position 12 of compounds of formula IV is esterified by treatment with 2-chloro acetic acid, DCC and DMAP or with 2-chloro acetic anhydride, pyridine, DMAP in a chlorinated solvent such as methylene chloride. The intermediate V is then treated with the appropriate nucleophile R1H in acetone in the presence of a base such as DBU to give compounds of formula VI wherein R1, $Rp_1$ and $Rp_2$ are as defined above. Depending on the nature of R1 compounds of formula VI can also be synthesised by reacting compound of formula IV with an appropriate carboxylic acid ($R1CH_2COOH$), DCC and DMAP in a chlorinated solvent such as methylene chloride to give compounds of formula VI. Compounds of formula VI are treated with an alkali metal base such as NaH or potassium tert.-butoxide or LDA in an aprotic solvent such as DMF or THF to give compounds of formula VII as mixture of diastereoisomers in various ratios (scheme 1).

Compounds of formula VII wherein R1, $Rp_1$ and $Rp_2$ are as defined above are deprotected at the 2'-position with methanol at temperatures ranging from 20° C. to 60° C. during 2-5 days to give compounds of formula VIII (scheme 2). The 4"-hydroxyl group is deprotected by treatment of the compound with DBU in refluxing methanol for 3 to 12 hours (J. Antibiotics, 2001, 54(8), 664) or by treatment with guanidine/guanidinium nitrate in methanol/dichloromethane (Tetrahedron Letters 1997, 38(9), 1627) or with potassium carbonate in methanol or with a mixture of MeONa in methanol, preferably with DBU in refluxing methanol for 5 to 7 hours to give compounds of formula Ia.

Alternatively compounds of formula VII can be deprotected at the 2'- and the 4"-position simultaneously using one of the methods described above for the deprotection of the 4"-hydroxyl group to give compounds of formula Ia (scheme 2).

Scheme 2

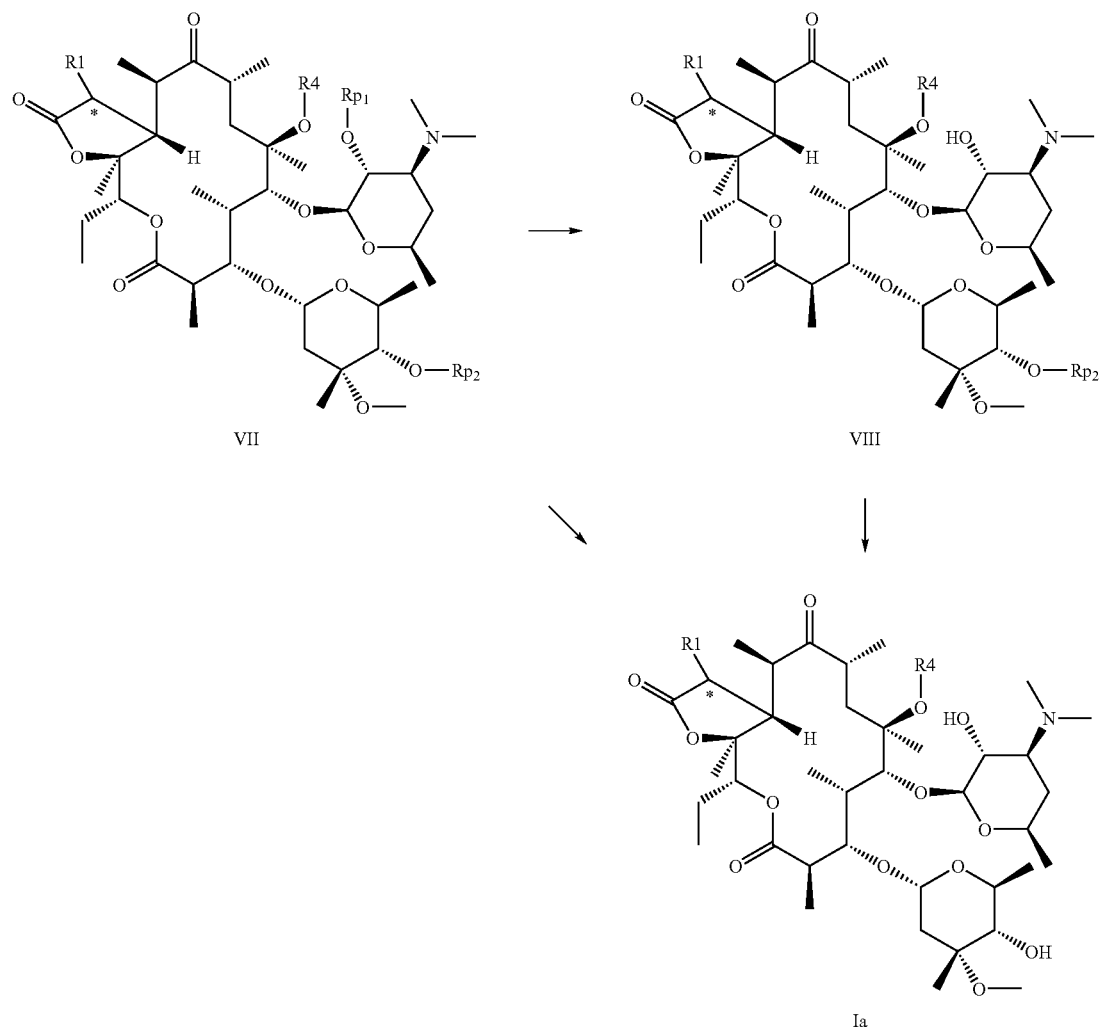

In the case where R1 is S-Rp$_3$ and Rp$_3$ is a sulphur protecting group e.g. benzyl, 4-methoxybenzyl, 3,4-dimethoxybenzyl or 4-nitro-benzyl, preferably 4-methoxybenzyl the intermediate VIIa is transformed in the presence of molecular sieves into disulfide derivative IX wherein Rp$_1$ and Rp$_2$ are as defined above and Rp$_4$ is e.g. 3-nitro-2-pyridinyl or methyl similar to the method described in WO03/072588.

Compounds of formula IX are treated with a reducing agent such as a trialkyl phosphine, preferably tributyl phosphine, or a triaryl phosphine, preferably triphenyl phosphine, in a solvent such as aqueous acetone, aqueous dimethyl formamide, aqueous dioxane or aqueous tetrahydrofuran, preferably aqueous dimethyl formamide, at 0° C. to 60° C., preferably at room temperature for 1 minute to 1 hour, preferably 15 minutes, to give compound X. Compound X is treated, preferably without isolation, directly in the same solvent system with compounds of the formula Q-X-Lg, in which Q and X are defined as before and Lg is a leaving group, e.g. chloride, bromide, iodide, methanesulfonyloxy, p-tosylsulfonyloxy, trifluormethansulfonyloxy or a vinyl group in the case where X represents a carbonyl or a sulfonyl group to give compounds of formula VII. The reaction is preferably effected in the presence of a base such as alkali metal carbonate or hydrogen carbonate, e.g. potassium carbonate, cesium carbonate or sodium hydrogen carbonate, or an organic base, e.g. triethylamine, N-ethyl N,N-diisopropylamine, 1,8-diazabicyclo[5.4.0]undec-7-ene or 1,5-diazabicyclo[4.3.0]non-5-ene, preferably 1,8-diazabicyclo[5.4.0]undec-7-ene at temperature between 0° C. and 50° C., preferably at 20° C. It can be advantageous to add catalytic amounts of an iodide salt, preferably sodium iodide, to the reaction mixture (Scheme 3).

Scheme 3

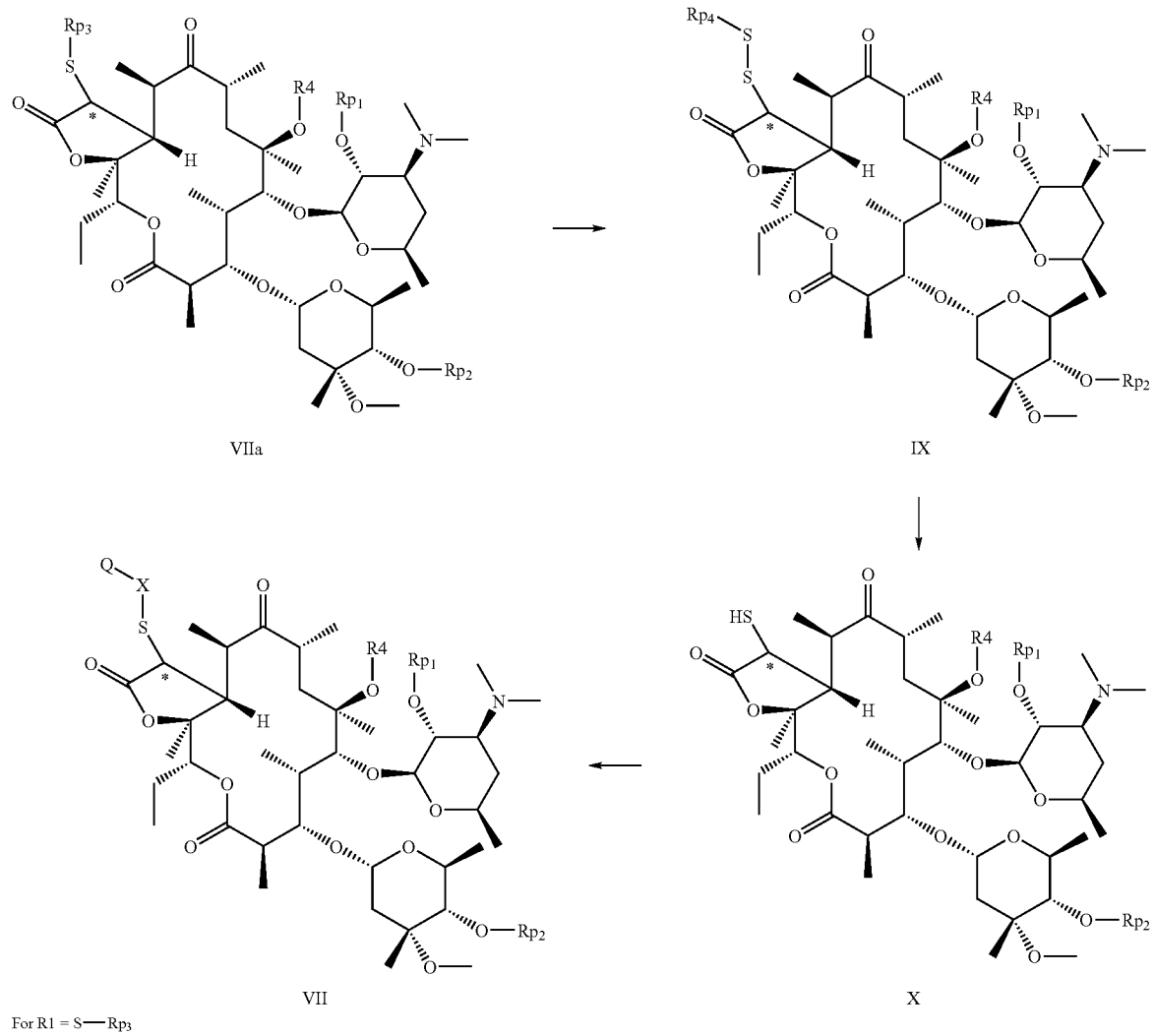

For R1 = S—Rp3

Alternatively, compounds of formula I, wherein R2 and R3 taken together form a group C═O and R4 has the meaning above and R1 is a residue —Y—X-Q, wherein X and Q have the same meaning as described above and Y is S; can also be prepared by a) converting a macrolide compound having the formula

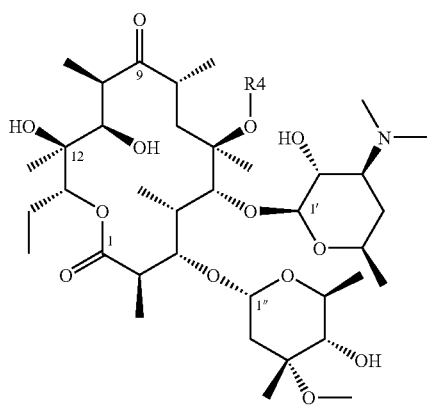

in a manner known per se to a compound of formula IV, e.g. as described above with regard to Scheme 1

IV

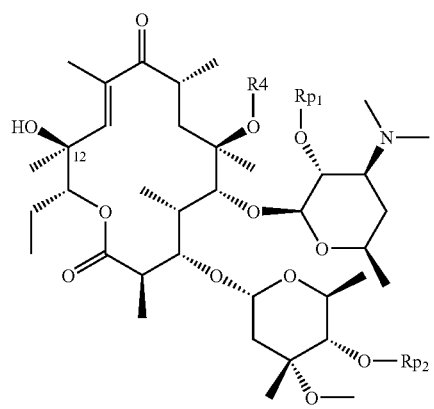

wherein $Rp_1$ and $Rp_1$ each are a hydroxyl protecting group and R4 is as defined above, b1) converting said compound of formula IV in the presence of an activated chloroacetic acid derivative, like e.g. di(chloroacetic acid) anhydride, in a manner known per se to a compound of formula V, e.g. as described above under Scheme 1

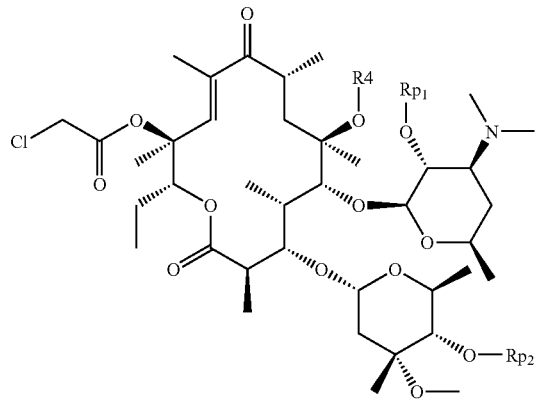

wherein $Rp_1$ and $Rp_2$ and R4 have the meaning above;

b2) further reacting said compound of formula V with a compound of formula

MS-X-Q, wherein M represents alkali metal atom and X and Q have the meaning described above, to form a compound of to a compound of formula VI

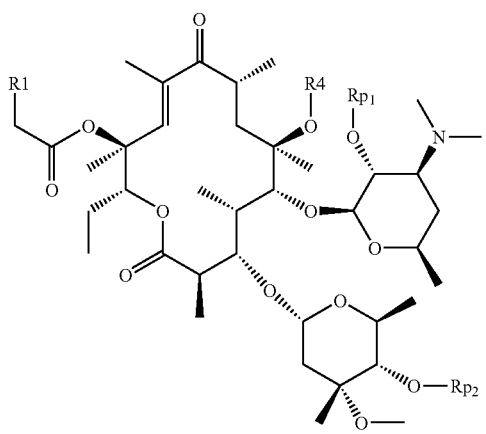

wherein R1 is —S—X-Q, and X, Q, $Rp_1$ and $Rp_2$ and R4 have the meaning above, c) reacting said compound of formula VI in an aprotic solvent with an alkali metal base to form a compound of formula VII

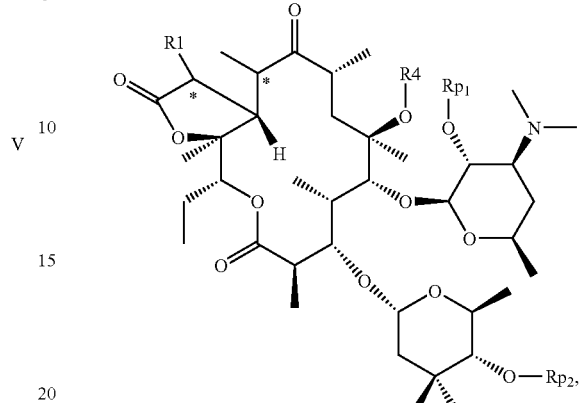

wherein R1 and $Rp_1$ and $Rp_2$ and R4 have the meaning above, and removing the hydroxyl protecting groups $Rp_1$ and $Rp_2$ simultaneously or consecutively to form the compound of formula I.

These compounds can be converted, if desired, in a manner known per se, e.g. as indicated in Scheme 5 to a compound of formula I wherein R2 is hydrogen and R3 is selected from hydroxyl or —O-(aliphatic group), said aliphatic group representing a saturated or unsaturated aliphatic group with 1 to 6 carbon atoms.

Compounds of formula Ic can e.g. be prepared by treatment of compounds of formula Ib (compound of formula I where Y=S) with 2 to 2.5 equivalent of 3-chloroperoxybenzoic acid (mCPBA) and 4 to 5 equivalent of $NaHCO_3$ in a solvent such as methylene chloride at temperatures ranging from 0° C. to room temperature preferably 0° C. during 1 hour to 3 hours. The N-oxide which is formed on the dimethylamino group of the sugar residue during the reaction is reduced at work-up by treating the organic phase with a aqueous solution of sodium pyrosulfite at room temperature during 5 minutes to 24 hours to give the desired compounds of formula Ic as a mixture of diastereoisomers. Alternatively, if appropriate, the N-oxide is reduced by catalytic hydrogenation according to standard procedures. Compounds of formula Ic can be further oxidised as described above but at room temperature during 1 to 48 hours to give, after reduction of the N-oxide, compounds of formula Id. Compounds Id can also be obtained in one step from compounds of formula Ib by using 3, 5 to 10 equivalent of the oxidising agent and 7 to 20 equivalent of $NaHCO_3$ at temperatures ranging from 0° C. to room temperature during 5 to 48 hours followed by the workup procedure described above (scheme 4).

In the case where Q is further substituted with oxidation sensitive substituents like amino groups, these substituents might need to be protected before submitting the sulfide Ia to oxidation. Suitable protecting groups commonly known in the art can be introduced according to standard procedures described in T. W. Green et al., Protective Groups in Organic Synthesis, John Wiley & Sons, 1999. After oxidation, the protecting group can be removed following standard procedures also described in T. W. Green et al.

Scheme 4
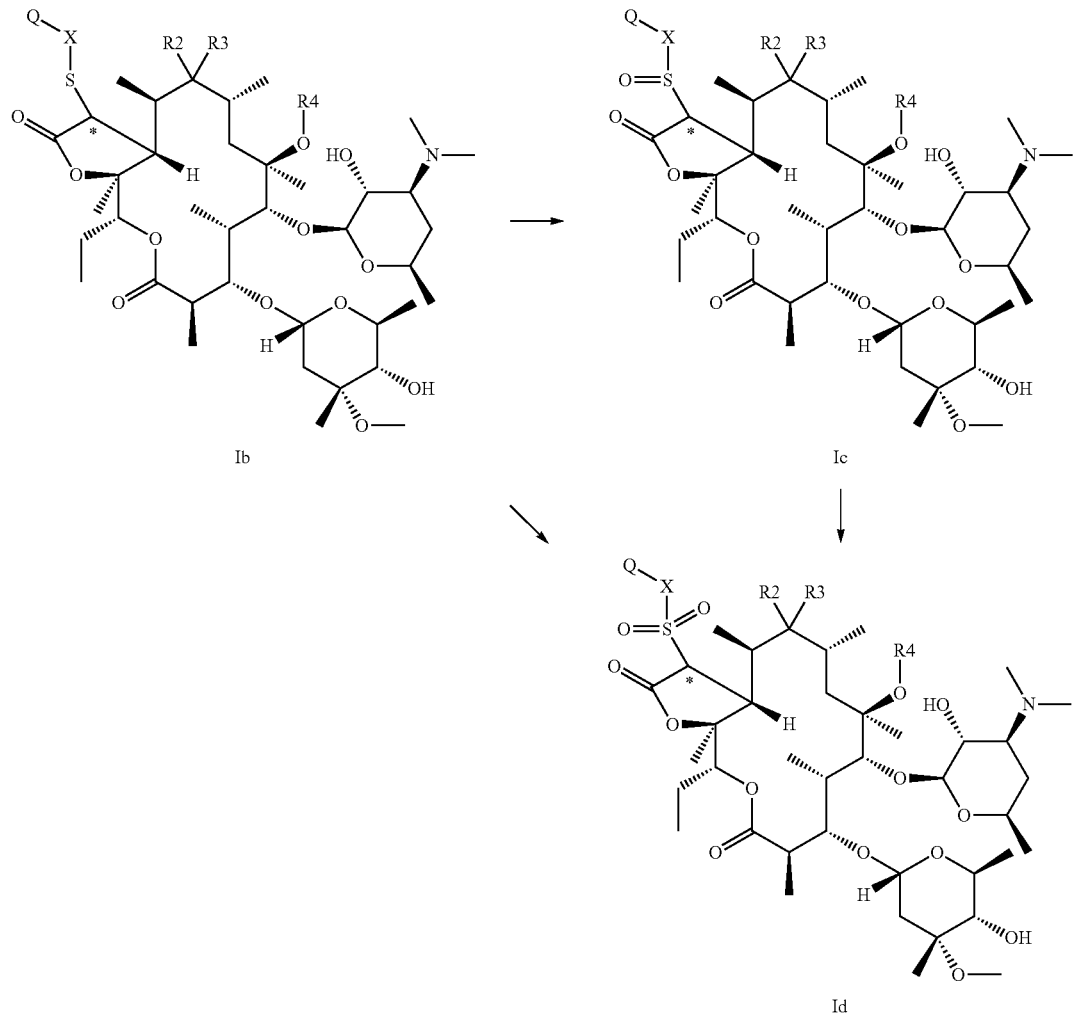
Scheme 5
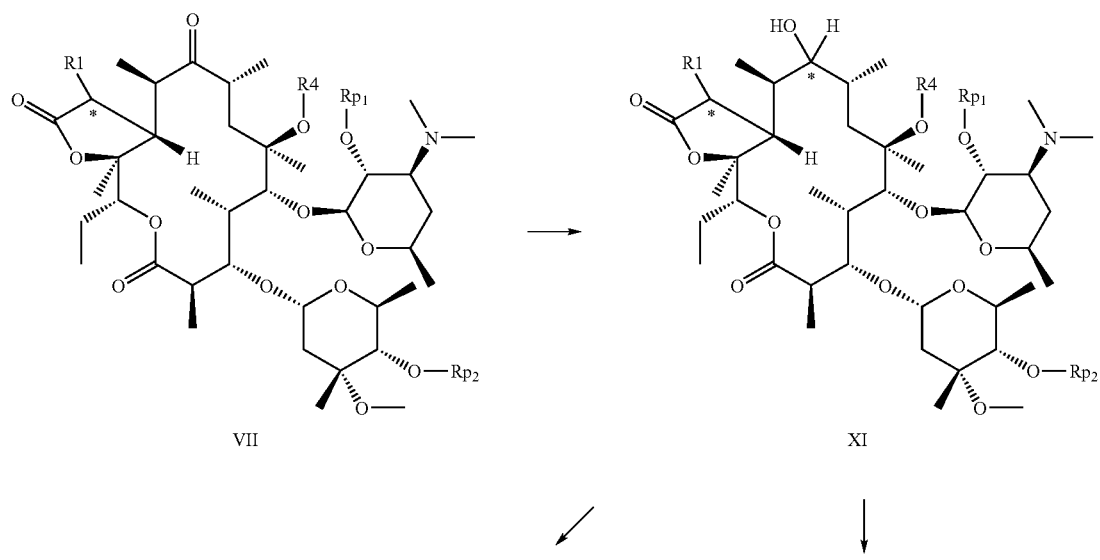

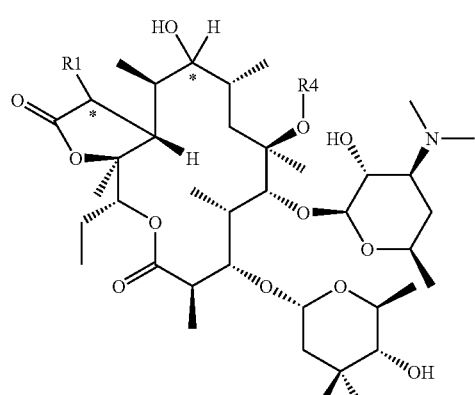

Ie

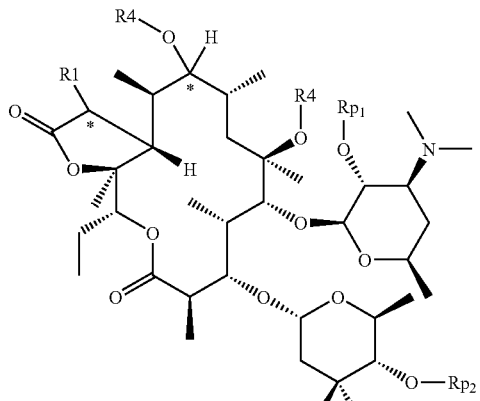

XII

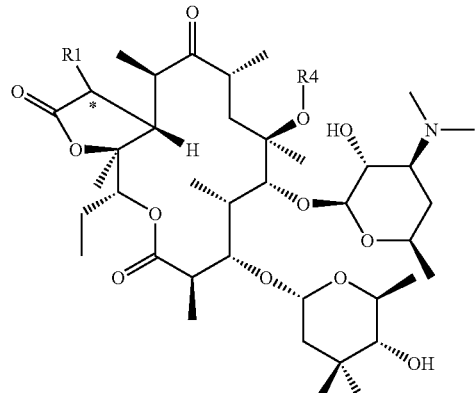

Ia

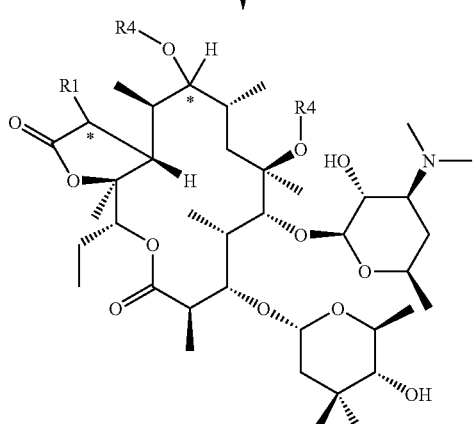

If

Compounds of formula XI can e.g. be prepared by treatment of compounds of formula VII with a reducing agent such as $NaBH_4$ in a solvent such as methanol, ethanol, isopropanol, THF, THF/water or diethylether at temperatures ranging from 0° C. to room temperature, preferably 0° C., during 1 hour to 24 hours. Compounds of formula XI are then deprotected as described above to obtain compounds of formula Ie. Alternatively, compounds of formula Ie can also be prepared starting from compounds of formula Ia following the method described for the reduction of compounds of formula VII. In the case where $Rp_1$ is acetyl the protecting group might get partially removed during reduction in a solvent such as methanol requiring a re-protection of the 2'-hydroxy group prior to the alkylation of the newly formed hydroxy group.

The hydroxyl group of compound of formula XI is alkylated following standard procedures known for the alkylation of hydroxyl groups to give compounds of formula XII. In the case where Q is further substituted with substituents that are alkylated under the conditions used for the transformation of XI into XII, these substituents might need to be protected before submitting compound XI to alkylation. Suitable protecting groups commonly known in the art can be introduced according to standard procedures described in T. W. Green et al., Protective Groups in Organic Synthesis, John Wiley & Sons, 1999. After alkylation, the protecting group can be removed following standard procedures also described in T. W. Green et al. Compounds of formula XII are deprotected following procedures described above to give compounds of formula If.

The following examples are given to further illustrate the invention and are not to be construed as in any way limiting the scope of the present invention.

A. EXAMPLES

General remarks: MS spectra were measured using (A) a Micromass Waters ZQ system with Masslynx software and (B) using a Q-T of-Ultima (Waters AG) equipped with the Waters Cap-LC. For accurate mass determination the nano lock mass ESI source was used. Accurate masses are given with four decimal digits. Analytical HPLC: System Aa: Instrument: Varian Prostar 210; column: Inertsil ODS-3V, 5 μm, 250×4 mm; flow: 1.0 mL/min; detection: 254 nm; mobile phase A: water; mobile phase B: acetonitrile; gradient: 0-5 min constant 5% acetonitrile; 5-25 min linear from 5% to 95% acetonitrile. System Ba: Instrument: Varian Prostar 210; column: Inertsil ODS-3V, 5 μm, 250×4 mm; flow: 1.0 mL/min; detection: 254 nm; column temp: 35° C.; mobile phase A: water+0.1% HCOOH; mobile phase B: acetonitrile+0.1% HCOOH; gradient: 0-5 min constant 5% B; 5-20 min linear from 5% to 95% B. HPLC purification of final products was done using the following systems: System Ap: Column: YMC ODS-AQ, 120A, 5 μm, 50×20 mm; precolumn: YMC ODS-AQ, 120A, 5 μm, 10×20 mm; flow: 30 ml/min; injection: 500 μl; detection: ELSD; mobile phase A: water+0.1% HCOOH; mobile phase B: acetonitrile; gradient: linear form 10 to 95% acetonitrile in 4 min. System Bp: Column: Purospher STAR RP18e, 5 μm, 125×25 mm flow: 25 mL/min; detection: 254 nm; mobile phase A: water 25 mM ammonium formiate; mobile phase B: methanol; gradient: linear form 60% to 90% methanol in 10 min. System Cp: Column: Purospher STAR RP18e, 5 μm, 125×25 mm flow: 25 mL/min; detection: 254 nm; mobile phase A: water 25 mM ammonium formiate; mobile phase B: acetonitrile; gradient: linear form 20% to 50% acetonitirile in 10 min. Abbreviations: HPLC for high performance liquid chromatography; DMSO for dimethylsulphoxide; DBU for diazabicycloundecane; DCM for dichloromethane; DIPEA for diisopropylethylamine (Huenig's base); DMF for dimethylformamide; THF for tetrahydrofurane; DCC for dicyclohexylcarbodiimide; DMAP for 4-dimethylaminopyridine; EDC.HCl for N-(3-dimethylaminopropyl)-N'-ethylcarbodiimide hydrochloride; HOBt for 1-hydroxy-benzotriazol; HATU for 2-(1H-Azabenzotriazol-1-yl)-1,1,3,3-tetramethyluronium hexafluorophosphate; mCPBA for m-Chloroperbenzoic acid; KOtBu for potassium tert.-butylate; TBDMSCl for tert-butyl-dimethyl-silylchloride, TBAF for tetrabutylammoniumfluoride, MS for mass spectrometry; NMR for nuclear magnetic resonance; ESI for electrospray ionization.

-continued

| Example | R1[1] | R2[2] R3[2] | R4 |
|---|---|---|---|
| 9 | 4-amino-imidazo[4,5-c]pyridine-7-carboxamide with N-(methoxycarbonylmethyl) amide and N9-propylthio linker | =O | —CH₃ |
| 10 | 4-amino-imidazo[4,5-c]pyridine-7-carboxamide with N-(pyridin-4-yl) amide and N9-ethylthio linker | =O | —CH₃ |
| 11 | 4-amino-imidazo[4,5-c]pyridine-7-carboxamide with N-(3,5-dichloropyridin-4-yl) amide and N9-ethylthio linker | =O | —CH₃ |
| 12 | 6-amino-2-[(pyridin-3-ylmethyl)amino]-9H-purine with N9-ethylthio linker | =O | —CH₃ |
| 13 | 6-amino-2-[(pyridin-3-ylmethyl)amino]-9H-purine with N9-ethylthio linker (isomer) | =O | —CH₃ |

[1] the star (*) indicates the point of attachment of R1 to the rest of the molecule
[2] "=O" in the merged box for R2 and R3 means that R2 and R3 taken together form a carbonyl group with the carbon to which they are attached.

Example 1

Preparation of I-1, compound of formula I where R1 is [2-[6-Amino-8-(2-pyridin-3-yl-ethyl)-purin-9-yl]ethyl]thio, R2 and R3 taken together form a C=O group and R4 is methyl

A] Preparation of 2-(6-amino-8-bromo-purin-9-yl)ethanol

To a solution of 10 g 2-(6-amino-purin-9-yl)ethanol in 200 ml 0.5M AcONa/AcOH buffer pH 4 were added 4 ml of Br₂. The resulting mixture was stirred at room temperature for 8 hours. The precipitated product was isolated, washed with water and crystallized from ethanol to give 6.13 g (43%) of the desired compound.

B] Preparation of 2-(6-amino-8-(2-pyridin-3-yl-ethynyl)-purin-9-yl)ethanol

To a solution of 258 mg of 2-(6-amino-8-bromo-purin-9-yl)ethanol in a mixture of Et₃N and DMF were added under an atmosphere of argon 35 mg of Pd(PPh₃)₃Cl₂, 19 mg CuI and 150 mg 3-ethynylpyridine. The mixture was stirred under argon at 60° C. for 3 hours and over night at room temperature. The precipitate was isolated, washed with water and hot ethanol and dried to give 150 mg (53%) of the desired product.

C] Preparation of 2-(6-amino-8-(2-pyridin-3-yl-ethyl)-purin-9-yl)ethanol

To a suspension of 1.1 g of 2-(6-amino-8-(2-pyridin-3-yl-ethynyl)-purin-9-yl)ethanol in 400 ml methanol were added 2.0 g of Raney-nickel and the mixture was hydrogenated (4 atm) at 80° C. during 6 hours. After completion of the reaction the catalyst was removed and the solvent was evaporated. The crude product was purified by column chromatography on silica gel (CHCl₃:MeOH 9:1) to give 0.45 g (41%) of the desired product.

D] Preparation of 6-amino-9-(2-chloroethyl)-8-(2-pyridin-3-yl-ethyl)-purine 0.45 g of 2-(6-amino-8-(2-pyridin-3-yl-ethyl)-purin-9-yl)ethanol were cooled to −20° C. and 6 ml of SOCl₂ were added. The temperature was gradually risen to 50° C. and the mixture was stirred at this temperature for 12 hours. The excess of SOCl₂ was evaporated and the residue was taken up in dichloromethane washed with saturated aqueous NaHCO₃ dried over Na₂SO₄ and evaporated in vacuo. The crude product was purified by flash chromatography on silica gel (CHCl₃: MeOH 50:1) to give 40 mg (8%) of the desired product.
¹H-NMR (DMSO-d₆): 8.65 (s, 1H); 8.4 (s, 1H); 8.1 (s, 1H); 7.75 (d, 1H); 7.30 (m, 1H); 6.95 (s, 2H, —NH₂); 4.45 (t, 2H); 4.0 (t, 2H).

E] Preparation of Compound of formula II where Rp₁ and Rp₂ are acetyl and R4 is methyl (II-1)

To a solution of 25 g (33.4 mmol) clarithromycin and 1.63 g (13.4 mmol) DMAP in 50 ml DCM were added 11 ml (117 mmol) acetic anhydride in one portion and the mixture was stirred for 20 h at room temperature. The reaction mixture was poured into enough 0.2 N NaOH to get a pH value of 8-9 and then extracted. The combined organic layers were washed with water and brine, dried over MgSO₄ and evaporated under

F] Preparation of Compound of Formula III where Rp₁ and Rp₂ are acetyl and R4 is methyl (III-1)

24.3 g (29.2 mmol) of 2',4"-di-O-acetyl-6-O-methylerythromycin A (II-1) were dissolved in 500 ml THF at −45° C. under argon and treated dropwise with 29.2 ml of a 1 M solution of sodium bis(trimethylsilyl)amide in tetrahydrofurane (29.2 mmol) over 15 min. After 20 min. at −45° C. 16.24 g (100.1 mmol) carbonyldiimidazole were added in 3 portions over 5 min. The reaction mixture was stirred at −45° C. for 30 min, then warmed to 0° C. over a period of 15 min and kept at 0° C. for 2.5 hours.

The reaction mixture was treated with a saturated aqueous solution of NaHCO₃ and water (1:1) and extracted twice with ethyl acetate. The combined organic layers were washed twice with 10% aqueous ammonia solution, with brine, dried over sodium sulfate and evaporated under reduced pressure to afford 23.57 g (94%) of a colorless solid. MS (ESI): 858.6 [MH]⁺.

G] Preparation of Compound of Formula IV where Rp₁ and Rp₂ are Acetyl and R4 is Methyl (IV-1)

23.5 g (27.47 mmol) of compound III-1 and 10.25 ml (68.7 mmol) DBU dissolved in 500 ml toluene were heated at reflux temperature for 1.5 h, cooled to room temperature and poured into 0.5 M aqueous NaH₂PO₄. The aqueous layer was extracted twice with ethyl acetate. The combined organic extracts were washed with 0.5 M NaH₂PO₄, brine, dried over Na₂SO₄ and concentrated to give 18.43 g (86%) of a colourless solid. MS (ESI): 814.5 [MH]⁺.

H] Preparation of Compound of Formula V where Rp₁ and Rp₂ are Acetyl and R4 is Methyl (V-1)

To a solution of 64.0 g (78.6 mmol) of compound IV-1, 3.84 g (31.4 mmol) 4-dimethylaminopyridine and 12.5 g of pyridine in 600 ml dichloromethane was added dropwise a solution of 26.9 g of chloroacetic acid anhydride (157.3 mmol) in 250 ml dichloromethane over 2 hours under nitrogen. The solution was stirred at room temperature for 3.5 hours. The reaction mixture was poured into 0.2N NaOH to get to a pH value of 8-9 and extracted twice with dichloromethane. The combined organic layers were washed successively with water, twice with 0.5N NaH₂PO₄, with water and twice with brine, dried over Na₂SO₄ and evaporated to give crude product. Petroleum ether was added to the crude product, the mixture was stirred for 3 hours at room temperature and filtered to give the title compound (57.5 g, 82%) as a light brownish solid. MS (ESI): 890.3.

I] Preparation of Compound of Formula VI where R1 is [(4-methoxyphenyl)methyl]thio and Rp₁ and Rp₂ are Acetyl and R4 is Methyl (VI-1)

10.5 g of compound V-1 were dissolved under argon in 180 ml acetone and 2.42 g DBU, 20 mg sodium iodide and 2.20 g (4-methoxyphenyl)methanethiol were added in one portion. The reaction mixture was stirred under argon at room temperature for 2.5 hours. 250 ml of DCM were added to the reaction mixture. The organic layer was washed three times with 5% NaHCO₃, dried over Na₂SO₄ and evaporated in vacuo to give 11.7 g (98.4%) of a light brown foam. MS (ESI): 1008.4.

K] Preparation of Compound of Formula VII where R1 is [(4-methoxyphenyl)methyl]thio and Rp₁ and Rp₂ are Acetyl and R4 is Methyl (VII-1)

6.00 g of compound of VI-1 were dissolved under nitrogen in 60 ml DMF and cooled with an ice bath. 0.39 g sodium hydride oil dispersion (60%) were added and the mixture was stirred during 3 hours at 0-5° C. Now aqueous KH₂PO₄ 0.5N were added and the mixture was extracted with 100 ml diethylether. The organic layer was washed three times with 60 ml aqueous NaHCO₃ 3% and with 80 ml brine, dried over Na₂SO₄ and evaporated in vacuo to afford 4.65 g crude product. MS (ESI): 1008.4 [MH]⁺.

L] Preparation of Compound of Formula I where R1 is [(4-methoxyphenyl)methyl]thio, R2 and R3 taken together form a C=O Group and R4 is Methyl 21.8 g (21.6 mmol) of crude compound VII-1 were dissolved in 290 ml methanol and 16.2 ml (108.3 mmol) DBU were added. The mixture was heated to reflux under argon for 5 hours. The solvent was evaporated under reduced pressure and the residue was taken up in 580 ml DCM. The organic layer was washed twice with water and with brine, dried over Na₂SO₄ and evaporated in vacuo. The crude product was washed with petroleum ether/diethylether 5/1. The residue was dissolved in 150 ml methanol and 55 ml of water were added. The mixture was stirred during 2 hours and the product was isolated by filtration to afford 11.1 g (41%) of the title compound as a solid. MS (ESI): 924.4.

M] Preparation of Compound of Formula VIIa where Rp₃ is (4-methoxyphenyl)methyl and Rp₁ is Acetyl, Rp₂ is Hydrogen and R4 is Methyl (VIIa-1)

2.0 g (2.16 mmol) of the product of example 1 step L were dissolved in 50 ml DCM and 0.22 ml (2.4 mmol) acetic anhydride were added. The mixture was stirred at room temperature for 48 hours. The solution was washed with aqueous NaHCO₃ (5%) and brine, dried over Na₂SO₄, filtered and concentrated in vacuo to give 2.17 g of a light brown foam. The crude product was used without purification for the next step. MS (ESI): 967.3 [MH]⁺.

N] Preparation of Compound of Formula IX where Rp₄ is Methyl, Rp₁ is Acetyl, Rp₂ is Hydrogen and R4 is Methyl (IX-1)

2.17 g (2.25 mmol) of VIIa-1 were dissolved in 50 ml DCM and molecular sieves was added. 880 mg (4.49 mmol) dimethyl(methylthio) sulfonium tetrafluoroborate were added to the mixture and the reaction was stirred for 5 hours at room temperature. The reaction mixture was filtered and washed twice with 20 ml aqueous NaHCO₃ (5%) and brine, dried over Na₂SO₄, filtered and concentrated in vacuo to give 1.62 g of a light brown foam. The crude product was used without purification for the next step. MS (ESI): 893.1 [MH]⁺.

O] Preparation of Compound of Formula VII where R1 is [2-[6-amino-8-(2-pyridin-3-yl-ethyl)-purin-9-yl]ethyl]thio, Rp₁ is Acetyl, Rp₂ is Hydrogen and R4 is Methyl (VII-1)

To a solution of 0.120 g (0.13 mmol) of the product of example 1 step N dissolved in 4 ml DMF and 1 drop of water, 66.4 µl (0.27 mmol) of tributylphosphine were added and the mixture was stirred for 30 min at room temperature. Then 44.8 mg (0.15 mmol) of 6-amino-9-(2-chloroethyl)-8-(2-pyridin-3-yl-ethyl)-purine and 40.2 µl DBU (0.27 mmol) were added to the solution. The reaction was stirred over night at room temperature and concentrated in vacuo and the residue was taken up in DCM. The organic layer was washed with aqueous NaHCO$_3$ (5%) and brine, dried over Na$_2$SO$_4$, filtered and concentrated in vacuo to give the crude product. The crude product was purified by flash chromatography on silica gel (DCM/MeOH/NH$_3$ 99:1:0.01→95:5:0.01) to give 57 mg (38%) of the desired product. MS (ESI): 1112.6 ([MH]$^+$), 577.0 ([MH$_2$]$^{++}$).

P] Preparation of Compound of Formula I where R1 is [2-[6-Amino-8-(2-pyridin-3-yl-ethyl)-purin-9-yl] ethyl]thio, R2 and R3 taken together form a C=O Group and R4 is Methyl (I-1)

The product of example 1 step O (54 mg) was dissolved in 2 ml methanol and stirred for 96 hours at room temperature. Then reaction mixture was concentrated in vacuo and the residue was purified by HPLC to afford the desired product as a white solid.
MS: accurate mass (ESI): 1069.5792 Da.

Example 2

Preparation of I-2, compound of formula I where R1 is [2-[6-Amino-8-(pyridin-3-ylamino)-purin-9-yl] ethyl]thio, R2 and R3 taken together form a C=O Group and R4 is Methyl A] Preparation of 6-amino-8-bromo-9-[2-(tert-butyl-dimethyl-silanyloxy)-ethyl]-purine To a solution of 3.0 g of 2-(6-amino-8-bromo-purin-9-yl) ethanol (example 1, step A) in 30 ml DMF were added 2.8 g TBDMSCl and 1.1 g imidazole and the mixture was stirred for 24 hours under argon at 20° C. The precipitate was filtered off, washed with water and dried to give 3.6 g (84%) of the desired product.

B] Preparation of 6-amino-8-(pyridin-3-ylamino)-9-[2-(tert-butyl-dimethyl-silanyloxy)ethyl]-purine To a solution of 0.372 g of the product of example 2, step A and 0.23 g 3-aminopyridine in 10 ml toluene were added 0.091 g Pd$_2$(dba)$_3$, 0.14 g t-BuONa and 0.087 g 9,9-dimethyl-4,5-bis(diphenylphosphino)xanthene (Xantphos). The mixture was stirred at 100° C. under an atmosphere of argon during 16 hours. After completion of the reaction the mixture was diluted with water and extracted with DCM. The organic layer was concentrated and the crude product was purified by flash chromatography on silica gel (CHCl$_3$:MeOH 20:1) to afford 0.1 g (26%) of the desired product.

C] Preparation of 2-(6-amino-8-(pyridin-3-ylamino)-purin-9-yl)ethanol

To a solution of 0.46 g of the product of example 2, step B in 10 ml THF were added 0.12 g of TBAF*3H$_2$O and the mixture was stirred during 16 hours at 20° C. The reaction mixture was subsequently concentrated and the crude product was purified by flash chromatography on silica gel (ethyl acetate:methanol 20:1) to afford 0.19 g (59%) of the desired product.

D] Preparation of 6-amino-9-(2-chloroethyl)-8-(pyridin-3-ylamino)-purine 0.11 g of 2-(6-amino-8-(pyridin-3-ylamino)-purin-9-yl) ethanol were cooled to −20° C. and 2 ml of SOCl$_2$ were added. The temperature was gradually risen to 50° C. and the mixture was stirred at this temperature for 12 hours. The excess of SOCl$_2$ was evaporated and aqueous ammonia was added to the residue. The mixture was extracted with ethyl acetate. The organic layer was separated and evaporated. The crude product was purified by flash chromatography on silica gel (ethyl acetate:MeOH 20:1) to give 30 mg (27%) of the desired product. $^1$H-NMR (DMSO-d$_6$): 9.10 (s, 1H); 9.0 (s, 1H); 8.35 (d, 1H); 8.20 (d, 1H); 8.05 (s, 1H); 7.30 (m, 1H); 6.65 (s, 2H, —NH$_2$); 4.55 (t, 2H); 4.0 (t, 2H).

E] Preparation of Compound of formula I where R1 is [2-[6-Amino-8-(pyridin-3-ylamino)-purin-9-yl] ethyl]thio, R2 and R3 taken together form a C=O Group and R4 is Methyl (I-2)

The title compound I-2 was prepared starting from 6-amino-9-(2-chloroethyl)-8-(pyridin-3-ylamino)-purine and IX-1 following the procedures described in example 1 steps O-P.
MS: accurate mass (ESI): 1056.5548 Da.

Example 3

Preparation of I-3, Compound of Formula I where R1 is [2-[(3cyclopentyloxy-4-methoxy-phenyl)-(pyridin-4-yl-carbonyl)-amino]ethyl]thio, R2 and R3 taken together form a C=O Group and R4 is Methyl A] Preparation of N-(3-cyclopentyloxy-4-methoxy-phenyl)-isonicotinamide 7.0 g (33.8 mmol) of 3-cyclopentyloxy-4-methoxy-phenylamine (Garcia et al., JOC, 2005, 70, p 1050) were dissolved in 150 ml of DCM. The solution was cooled to 0° C. and 5.74 g (40.5 mmol) isonicotinoyl chloride in 50 ml DCM were added to the solution. A precipitate was formed. The reaction mixture was subsequently stirred at room temperature during two hours. A solution of 2.7 g NaOH in 100 ml water was added to the reddish reaction mixture. The organic layer was separated, dried over Na$_2$SO$_4$ and evaporated. The crude product was purified by flash chromatography on silica gel (ethyl acetate/n-hexane 2:1) to afford 7.2 g (62%) of the desired product. MS (ESI): 313.1.

B] Preparation of N-(2-chloroethyl)-N-(3-cyclopentyloxy-4-methoxy-phenyl)-isonicotinamide 3.0 g (9.6 mmol) of the product of example 3 step A were dissolved in 50 ml 1-bromo-2-chloroethane and 5.33 g (95 mmol) of potassium hydroxide were added to the solution. The reaction mixture was stirred at room temperature over night and then heated to 60° C. for four hours. The reaction mixture was cooled to room temperature and 50 ml water were added. The mixture was extracted with 50 of DCM. The organic layer was washed with water and brine, dried over Na$_2$SO$_4$ and evaporated. The crude product was purified by flash chromatography on silica gel (ethyl acetate/n-hexane 1:1) to afford 1.3 g (43%) of the desired product as a yellow oil. $^1$H-NMR (DMSO-d$_6$): 8.45 (d, 2H); 7.21 (d, 2H); 6.8 (m, 3H); 4.63 (m, 1H); 4.13 (t, 2H); 3.76 (t, 2H); 3.66 (s, 3H); 1.4-1.8 (m, 8H).

C] Preparation of Compound of Formula I where R1 is [2-[(3cyclopentyloxy-4-methoxy-phenyl)-(pyridin-4-yl-carbonyl)-amino]ethyl]thio, R2 and R3 taken together form a C=O Group and R4 is Methyl (I-3)

The title compound I-3 was prepared starting from N-(2-chloroethyl)-N-(3-cyclopentyloxy-4-methoxy-phenyl)-isonicotinamide and IX-1 following the procedures described in example 1 steps O-P.
MS: accurate mass (ESI): 1141.6073 Da.

Example 4

Preparation of I-4, compound of formula I where R1 is [2-[(3-cyclopentyloxy-4-methoxy-phenyl)-(pyridin-4-ylmethyl)-amino]-ethyl]thio, R2 and R3 taken together form a C=O Group and R4 is Methyl A] Preparation of (3-cyclopentyloxy-4-methoxy-phenyl)-(pyridin-4-ylmethyl)-amine 0.5 g (1.6 mmol) of the product of example 3 step A was dissolved under nitrogen in 20 ml dry THF and 0.24 g (6.4 mmol) lithium aluminium hydride were added at room temperature. The reaction mixture was stirred for two hours at room temperature and then cooled to 0° C. and 2 ml of water were added. The mixture was extracted with 3×20 ml of ethyl acetate. The combined organic layers were washed with water and brine, dried over $Na_2SO_4$ and evaporated in vacuo to give the crude product as an oil. The crude product was purified by flash chromatography on silica gel (ethyl acetate/n-hexane 1:1) to afford 0.4 g (84%) of the desired product as an oil. MS (ESI): 299.2 ([MH]$^+$).

B] Preparation of (2-chloro-ethyl)-(3-cyclopentyloxy-4-methoxy-phenyl)-(pyridin-4-ylmethyl)-amine 3.85 g (12.9 mmol) of the product of example 4 step A were dissolved in 50 ml methanol at 25° C. and 5.1 ml of a solution of chloroacetaldehyde (40% in water; 77.4 mmol, 6 eq), 4.86 g (77.4 mmol, 6. eq) of sodium cyano borohydride and 0.74 ml (12.9 mmol) of acetic acid were added. The mixture was stirred at 25° C. for 16 hours. Then the solvent was removed under reduced pressure and the residue was taken up in 100 ml dichloromethane. The mixture was washed with 3×50 ml brine, dried over $Na_2SO_4$ and evaporated in vacuo. The crude product was purified by flash chromatography on silica gel (ethyl acetate/n-hexane 1:4) to afford 1.66 g (35%) of the desired product as an oil.
MS (ESI): 361.2, 363.1 ([MH]$^+$).
$^1$H-NMR (CDCl$_3$): 8.52 (d, 2H); 7.17 (d, 2H); 6.75 (d, 1H); 6.18-6.24 (m, 2H); 4.6 (m, 1H); 4.52 (s, 2H); 3.75 (s, 3H); 3.64-3.73 (m, 4H); 1.5-1.9 (m, br, 8H).

C] Preparation of Compound of Formula IX where Rp$_4$ is Methyl, Rp$_1$ and Rp$_2$ are Hydrogen and R4 is Methyl (IX-4)

3.1 g (3.35 mmol) of the product of example 1 step L were dissolved in 80 ml DCM and molecular sieves was added. 1.0 g (4.94 mmol) dimethyl(methylthio) sulfonium tetrafluoroborate were added to the mixture and the reaction was stirred for 20 hours at room temperature. The reaction mixture was filtered and the filtrate was washed twice with 80 ml aqueous NaHCO$_3$ (5%), 80 ml water and 80 ml brine, dried over $Na_2SO_4$, filtered and concentrated in vacuo to give 3.04 g of a light brown foam. The crude product was used without purification for the next step.
MS (ESI): 850.2 [MH]$^+$.

D] Preparation of Compound of Formula I where R1 is [2-[(3-cyclopentyloxy-4-methoxy-phenyl)-(pyridin-4-ylmethyl)-amino]-ethyl]thio, R2 and R3 taken together form a C=O Group and R4 is Methyl. (I-4)

To a solution of 0.136 g (0.16 mmol) of the product of example 4 step C dissolved in 7.5 ml DMF and 35 μl of water, 80 μl (0.32 mmol) of tributylphosphine were added and the mixture was stirred at room temperature until no starting material remained (3 hours). Then 45 mg (0.24 mmol) of the product of example 4 step B and 36 μl DBU (0.24 mmol) were added to the solution. The reaction was stirred for 13 hours at room temperature and then 15 ml of water were added and the mixture was extracted with 3×20 ml ethyl acetate. The combined organic layers were concentrated, dried over $Na_2SO_4$, filtered and concentrated in vacuo to give the crude product as yellow oil. An initial purification of the product was done by flash chromatography on silica gel (ethyl acetate/hexane 5/1). The compound was further purified by preparative HPLC (column: Xterra C18(5 μm) 100 mm×10 mm; mobile phase A: water+0.02% NH$_4$OH, mobile phase B: MeOH; flow rate: 10 ml/min; detection: 254 nm; gradient: 0 min/90% A/10% B, 10 min/40% A/60% B,
10.1 min/0% A/100% B).
MS: accurate mass (ESI): 1128.6423 Da.
Ret. Time: 10.8 min. (column: Prontosil 120-3-C18 SH 3 μm, 75×4.6 mm; flow: 1.0 mL/min; detection: 254 nm; column temp: rt; mobile phase A: water+0.1% TFA; mobile phase B: methanol; gradient: 0-5 min constant 30% B; 5-25 min linear from 30% to 95% B).

Example 5

Preparation of I-5, Compound of Formula I where R1 is [2-[(3-cyclopentyloxy-4-methoxy-phenyl)-(pyridin-3-ylmethyl)-amino]-ethyl]thio, R2 and R3 taken together form a C=O Group and R4 is Methyl A] Preparation of N-(3-cyclopentyloxy-4-methoxy-phenyl)-nicotinamide 3.2 g (14.3 mmol) of 3-cyclopentyloxy-4-methoxy-phenylamine (Garcia et al., JOC, 2005, 70, p 1050) were dissolved in 120 ml of DCM. The solution was cooled to 0° C. and 15 ml (107.6 mmol, 7.5 eq.) triethylamine and 3.7 g (26.1 mmol; 1.8 eq) nicotinoyl chloride in 50 ml DCM were added to the reaction mixture. The reaction mixture was stirred for 2 h and then a solution of 1.3 g NaOH in 50 ml water was added to the mixture. The organic phase was separated and washed with water and brine, dried over $Na_2SO_4$ and evaporated in vacuo. The crude product was purified by flash chromatography on silica gel (ethyl acetate/n-hexane 1:1) to afford 4 g (85%) of the desired product as a white solid.
MS (ESI): 313.0 ([MH]$^+$).
$^1$H-NMR (DMSO-d$_6$): 10.24 (s, 1H); 9.07 (s, 1H); 8.73 (d, 1H); 8.25 (d, 1H); 7.54 (dd, 1H); 7.42 (s, 1H); 7.29 (d, 1H); 6.91 (d, 1H); 4.70 (m, 1H); 3.71 (s, 3H); 1.56-1.90 (m, 8H).

B] Preparation of (3-cyclopentyloxy-4-methoxy-phenyl)-(pyridin-3-ylmethyl)-amine 0.5 g (1.6 mmol) of the product of example 5 step A was dissolved under nitrogen in 20 ml dry THF and 0.24 g (6.4 mmol) lithium aluminium hydride were added at 0° C. The reaction mixture was stirred for two hours at 15° C. and then cooled to 0° C. and 2 ml of water were added. The mixture was extracted with 3×20 ml of ethyl acetate. The combined organic layers were washed with water and brine, dried over $Na_2SO_4$ and evaporated in vacuo to give the crude product as an oil. The crude product was purified by flash chromatography on silica gel (ethyl acetate/n-hexane 1:1) to afford 180 mg (38%) of the desired product as a light yellow oil. MS (ESI): 299.1 ([MH]$^+$).

$^1$H-NMR (DMSO-d$_6$): 8.54 (s, 1H); 8.41 (d, 1H); 7.72 (d, 1H); 7.32 (dd, 1H); 6.64 (d, 1H); 6.22 (d, 1H); 6.02 (dd, 1H); 4.60 (m, 1H); 4.21 (s, 2H); 3.56 (s, 3H); 1.50-1.76 (m, 8H).

C] Preparation of (2-chloro-ethyl)-(3-cyclopentyloxy-4-methoxy-phenyl)-(pyridin-3-ylmethyl)-amine 150 mg (0.51 mmol) of the product of example 5 step B were dissolved in 10 ml methanol at 25° C. and 0.5 ml of a solution of chloroacetaldehyde (40% in water; 7.74 mmol, 15 eq), 0.25 g (3.98 mmol, 7.8 eq) of sodium cyano borohydride and 0.05 ml (0.87 mmol) of acetic acid were added. The mixture was stirred at 15° C. for 4 hours. Then the solvent was removed under reduced pressure and the residue was taken up in 100 ml dichloromethane. The mixture was washed with 3×50 ml brine, dried over $Na_2SO_4$ and evaporated in vacuo. The crude product was purified by flash chromatography silica gel (ethyl acetate/n-hexane 1:4) to afford 140 mg (35%) of the desired product as a light yellow oil. MS (ESI): 361.2, 363.1 ([MH]$^+$).

$^1$H-NMR (DMSO-d$_6$): 8.45 (s, 1H); 8.39 (d, 1H); 7.58 (d, 1H); 7.29 (dd, 1H); 6.72 (d, 1H); 6.25 (s, 1H); 6.20 (d, 1H); 4.62 (m, 1H); 4.60 (s, 2H); 3.74 (t, 2H); 3.71 (t, 2H); 3.58 (s, 3H); 1.46-1.67 (m, 8H).

D] Preparation of Compound of Formula I where R1 is [2-[(3-cyclopentyloxy-4-methoxy-phenyl)-(pyridin-3-ylmethyl)-amino]-ethyl]thio, R2 and R3 taken together form a C=O Group and R4 is Methyl (I-5)

The title compound I-5 was prepared starting from (2-chloro-ethyl)-(3-cyclopentyloxy-4-methoxy-phenyl)-pyridin-3-ylmethyl-amine (example 5 step C) and IX-4 following the procedure described in example 4 step D.

The product was first purified by preparative HPLC with system Bp. The isolated product was dissolved in DCM and washed with diluted aqueous NaOH. The organic layer was dried and evaporated. This product was further purified by HPLC (system Ap).

MS: accurate mass (ESI): 1128.6434 Da.
Ret. Time (system Aa): 16.7 min.

Example 6

Preparation of I-6, compound of formula I where R1 is [2-[(5-(3,5-dichloro-pyridin-4-yl-amino-carbonyl)-1-ethyl-1H-pyrazolo[3,4-b]pyridin-4-ylamino]-ethyl]thio, R2 and R3 taken together form a C=O Group and R4 is Methyl A] Preparation of 4-(2-chloro-ethylamino)-1-ethyl-1H-pyrazolo[3,4-b]pyridine-5-carboxylic acid ethyl ester 2.54 g (10 mmol) of 4-chloro-1-ethyl-1H-pyrazolo[3,4-b]pyridine-5-carboxylic acid ethyl ester (*J. Med. Chem.* 2001, 44, 1025) and 1.28 g (11 mmol) 2-chloroethylamine hydrochloride were added to 40 ml of anhydrous ethanol. Then 7 ml (50 mmol) of triethylamine were added. The mixture was heated at reflux until the reaction was completed (4 hours). The reaction mixture was concentrated under reduced pressure and 20 ml of saturated aqueous sodium carbonate solution was added. The mixture was extracted with 3×20 ml ethyl acetate. The combined organic layers were washed with 15 ml of water and 15 ml of brine, dried over $Na_2SO_4$ and evaporated in vacuo. The crude product (2.88 g) was first purified by flash chromatography on silica gel (petrol ether/ethyl acetate 5:1) and then crystallized from 20 ml of hexane/ethyl acetate=1/1 to afford 1.24 g (42%) of the desired product as a white crystalline solid.

MS (ESI): 297.1 ([M+H]$^+$).
$^1$H-NMR (CDCl$_3$): 9.70 (broad, 1H), 8.90 (s, 1H), 8.04 (s, 1H), 4.54 (q, 2H), 4.36 (q, 2H), 4.03 (t, 2H), 3.87 (t, 2H), 1.50 (t, 3H), 1.40 (t, 3H).

B] Preparation of 4-(2-chloro-ethylamino)-1-ethyl-1H-pyrazolo[3,4-b]pyridine-5-carboxylic acid A solution of 1.17 g (4.0 mmol) of the product of example 6 step A in 15 ml ethanol was added to a solution of 0.64 g (16.0 mmol) of NaOH in 2 ml water. The resulting mixture was heated at reflux for 3 hours. Ethanol was removed under reduced pressure and 10 ml of water was added to the residue. The solution was acidified to pH 5 with HCl 2N leading to precipitation of the product. The precipitate was isolated by filtration and dried to afford 0.5 g (44%) of the desired product as a white solid.

MS (ESI): 269.1 ([M+H]$^+$).
$^1$H-NMR (CDCl$_3$):12.75 (b, 1H), 9.54 (s, 1H), 8.68 (s, 1H), 8.19 (s, 1H), 4.36 (q, 2H), 4.05 (t, 2H), 3.93 (t, 2H), 1.34 (t, 3H).

C] Preparation of 4-(2-chloro-ethylamino)-1-ethyl-1H-pyrazolo[3,4-b]pyridine-5-carboxylic acid (3,5-dichloro-pyridin-4-yl)-amide 0.8 g (3.0 mmol) of the product of example 6 step B, 0.8 g (6 mmol) HOBt and 1.14 g (6 mmol) EDC.HCl were suspended in 25 ml THF and 2.1 g (21 mmol) triethylamine were added. The mixture was stirred at 15° C. until all starting material disappeared (24 hours). The solvent was removed under reduced pressure and the crude product was purified by column chromatography (petrol ether/ethyl acetate 4:1) to afford 0.64 g of a white solid. 131 mg NaH (60%, 5.7 mmol) was suspended in 15 ml THF and a solution of 3,5-dichloro-4-aminopyridine in 5 ml THF was added dropwise at 15° C. to this suspension. After 1 hour a solution of 570 mg (1.42 mmol) of the above-mentioned white solid in 5 ml THF was slowly added to this mixture and stirred for another 30 minutes. 0.1 ml of water was added to the reaction mixture and the solvent was evaporated. The residue was purified by flash chromatography on silica gel (petrol ether/ethyl acetate 4:1) to give 92 mg of the desired product. This product was recrystallised from acetone/hexane 1/2 to give 68 mg (11.6%) of the desired product as pale yellow solid.

MS (ESI): 413.0 ([M+H]$^+$).
$^1$H-NMR (CDCl$_3$): 9.68 (s, 1H), 8.77 (s, 1H), 8.56 (s, 2H), 8.06 (s, 1H), 7.91 (s, 1H), 4.53 (q, 2H), 4.03 (t, 2H), 3.82 (t, 2H), 1.52 (t, 3H).

D] Preparation of Compound of Formula I where R1 is [2-[(5-(3,5-dichloro-pyridin-4-yl-amino-carbonyl)-1-ethyl-1H-pyrazolo[3,4-b]pyridin-4-ylamino]-ethyl]thio, R2 and R3 taken together form a C=O Group and R4 is Methyl (I-6)

The title compound I-6 was prepared starting from 4-(2-chloro-ethylamino)-1-ethyl-1H-pyrazolo[3,4-b]pyridine-5- carboxylic acid (3,5-dichloro-pyridin-4-yl)-amide (product of example 6 step C) and IX-1 following the procedures described in example 1 steps O-P. the product was purified by HPLC (System Ap)

MS: accurate mass (ESI): 1180.5134 Da.

Example 7

Preparation of I-7, Compound of Formula I where R1 is [3-[2,3-dimethoxy-6-(pyridin-4-yl-amino-carbonyl)phenyl]-propyl]thio, R2 and R3 taken together form a C=O Group and R4 is Methyl A] Preparation of 1-(3-benzyloxy-propyl)-2,3-dimethoxy-benzene 2.50 g (62.5 mmol) NaH (60% in oil) were suspended under nitrogen in 70 ml dry THF and a solution of 7.1 g (36.2 mmol) 3-(2,3-dimethoxy-phenyl)-propan-1-ol (*J. Org. Chem.*, 1987, 52, 1072) in 50 ml THF was added dropwise at 18° C. The resulting mixture was stirred for 30 minutes and then a solution of 6.81 g (39.8 mmol) benzylbromide in 30 ml THF was added dropwise and the mixture was stirred over night at 18° C. The reaction was quenched with 10 ml water and the organic solvent was evaporated under reduced pressure. The residue was dissolved in 200 ml of ethyl acetate and the organic layer was washed with water and brine, dried over $Na_2SO_4$ and evaporated in vacuo. The crude product was purified by column chromatography on silica gel (ethyl acetate/n-hexane 1:40) to afford 8 g (77%) of the desired product as a colorless oil.

$^1$H-NMR (CDCl$_3$): 7.36-7.27 (m, 5H); 6.99-6.95 (m, 1H); 6.78-6.76 (m, 2H); 4.52 (s, 2H); 3.86 (s, 3H,); 3.81 (s, 3H); 3.52 (t, 2H); 2.73 (t, 2H); 1.93 (m, 2H).

B] Preparation of 1-(3-benzyloxy-propyl)-6-bromo-2,3-dimethoxy-benzene 8.0 g (27.9 mmol) of the product of example 7 step A were dissolved under nitrogen in 120 ml of DCM and 5.47 g (30.7 mmol) N-bromosuccinimide and 0.48 g (2.8 mmol) were added. The mixture was stirred over night at 18° C. The reaction mixture was concentrated in vacuo and the crude product was purified by column chromatography on silica gel (ethyl acetate/n-hexane 1:40) to give 9.7 g (95%) of the desired product as a colorless oil.

$^1$H-NMR (CDCl$_3$): 7.38-7.27 (m, 5H); 7.24 (d, 1H); 6.67 (d, 1H); 4.54 (s, 2H); 3.84 (s, 3H); 3.81 (s, 3H); 3.58 (t, 2H); 2.86 (t, 2H); 1.875 (m, 2H).

C] Preparation of 2-(3-benzyloxy-propyl)-3,4-dimethoxy-benzoic acid 9.7 g (26.7 mmol) of the product of example 7 step B were dissolved under nitrogen in 40 ml of dry THF. The solution was cooled to −78° C. and 18 ml of a solution of butyl-lithium (2.2M in n-hexane) were added. After 30 minutes 400 g of solid $CO_2$ were added and the reaction mixture was slowly warmed to room temperature. The reaction mixture was poured into water and the mixture was extracted with hexane. 20 ml of aqueous HCl 3M were added to the aqueous layer and extracted with 2×100 ml of ethyl acetate. The combined organic layer was washed with brine, dried over $Na_2SO_4$ and evaporated in vacuo to give 9 g of the crude product as white solid.

$^1$H-NMR (CDCl$_3$): 7.86 (d, 1H); 7.37-7.24 (m, 5H); 6.82 (d, 1H); 4.53 (s, 2H); 3.92 (s, 3H); 3.82 (s, 3H); 3.59 (t, 2H); 3.13 (t, 2H); 1.92 (m, 2H).

D] Preparation of 2-(3-benzyloxy-propyl)-N-(3,5-dichloro-pyridin-4-yl)-3,4-dimethoxy-benzamide 10.8 g (52.4 mmol) DCC and 5.0 g (37 mmol) HOBt were added to a solution of 8.7 g (26.3 mmol) of the product of example 7 step C in 150 ml DCM under an atmosphere of nitrogen and the mixture was stirred at 40° C. for 2 hours. The suspension was filtered and the filtrate was concentrated in vacuo. The resulting product was purified by column chromatography on silica gel (hexane/ethyl acetate 8/1) to give 8.5 g of a white solid. A solution of 4 g (8.9 mmol) of this white solid in 40 ml dry THF was added dropwise to a suspension of 1.6 g (9.8 mmol) 4-amino-3,5-dichloro-pyridine and 822 mg (35.8 mmol) NaH (60% in oil) in THF, which has been stirred at room temperature for 1.5 hours. The resulting mixture was stirred at 30° C. for 2 hours and then quenched with water. The mixture was extracted with 2×100 ml of ethyl acetate. The combined organic layers were washed with water and brine, dried over $Na_2SO_4$ and evaporated in vacuo. The crude product was purified by column chromatography on silica gel to give 4.1 g (96%) of the desired product as white solid.

$^1$H-NMR (DMSO-d$_6$): 8.47 (s, 2H); 8.39 (s, 1H); 7.43 (d, 1H); 7.26-7.17 (m, 5H); 6.88 (d, 1H,); 4.38 (s, 2H); 3.92 (s, 3H); 3.84 (s, 3H); 3.54 (t, 2H); 3.08 (t, 2H); 2.09 (q, 2H).

E] Preparation of 2-(3-hydroxy-propyl)-3,4-dimethoxy-N-pyridin-4-yl-benzamide 1.0 g (2.1 mmol) of the product of example 7 step D was dissolved in 200 ml of ethanol and 230 mg Pd/C (10%) were added. The mixture was stirred for 36 hours at room temperature under an atmosphere of hydrogen gas (40 psi). The catalyst was removed by filtration and the filtrate was concentrated under reduced pressure. The crude product was purified by column chromatography on silica gel to give 280 mg of the desired product as white solid.

MS (ESI): 317.1 ([MH]$^+$).

$^1$H-NMR (DMSO-d$_6$): 11.58 (s, 1H); 8.71 (d, 2H); 8.18 (d, 2H); 7.37 (d, 1H); 7.04 (d, 1H); 3.86 (s, 3H); 3.74 (s, 3H); 3.36 (t, 2H); 2.75 (t, 2H); 1.61 (q, 2H).

F] Preparation of 2-(3-chloro-propyl)-3,4-dimethoxy-N-pyridin-4-yl-benzamide 200 mg (0.63 mmol) of the product of example 7 step E and 163 mg (0.76 mmol) of PCl$_5$ were dissolved in 4 ml DCM and the resulting mixture was stirred at 20° C. for 30 minutes. The mixture was concentrated and the crude product was purified by column chromatography on silica gel (DCM/MeOH 10:1) to afford 160 mg (75%) of the desired product as a white solid.

MS (ESI): 335.1 ([MH]$^+$).

$^1$H-NMR (DMSO-d$_6$): 11.54 (s, 1H); 8.69 (d, 2H); 8.15 (d, 2H); 7.391 (d, 1H); 7.09 (d, 1H); 3.87 (s, 3H); 3.76 (s, 3H); 3.61 (t, 2H); 2.84 (t, 2H); 1.934 (q, 2H).

G] Preparation of Compound of Formula I where R1 is [3-[2,3-dimethoxy-6-(pyridin-4-yl-amino-carbonyl)phenyl]propyl]thio, R2 and R3 taken together form a C=O Group and R4 is Methyl (I-7)

The title compound I-7 was prepared starting from 2-(3-chloro-propyl)-3,4-dimethoxy-N-pyridin-4-yl-benzamide (example 7 step F) and IX-4 following the procedure described in example 4 step D. This product was purified by preparative HPLC (system Ap) to give a white solid.

MS: accurate mass (ESI): 1102.5927 Da.

Example 8

Preparation of I-8, compound of formula I where R1 is [3-[4-Amino-7-(pyridin-4-yl-amino-carbonyl)-imidazo[4,5-c]pyridin-1-yl]-propyl]thio, R2 and R3 taken together form a C=O Group and R4 is Methyl

A] Preparation of 4,6-dihydroxy-nicotinic acid ethyl ester

A mixture of 5.0 g (24.73 mmol) diethyl 1,3-acetonedicarboxylate, 5.05 g (49.45 mmol) acetic anhydride and 3.7 g (24.73 mmol) ethyl orthoformate was heated to 120° C. for 2 hours. Volatile components were removed under reduced pressure and the remaining mixture was treated with 10 ml of aqueous ammonia (25%). The mixture was stirred for 30 minutes at room temperature. Subsequently the pH of the mixture was adjust to pH 2 with aqueous HCl (2N). The solid was filtered off, washed with cold water and dried. 8 ml of toluene were added to the crude product, the mixture was stirred at 0° C. for 30 minutes and then filtered and dried to give 2.26 g (50%) of a red solid.

$^1$H-NMR (DMSO-d$_6$): 11.77 (s, br, 1H); 10.74 (s, br, 1H); 8.01 (s, 1H); 5.60 (s, 1H); 4.26 (q, 2H); 1.28 (t, 3H).

B] Preparation of 4,6-dihydroxy-5-nitro-nicotinic acid ethyl ester

To a solution of 2.34 g (12.78 mmol) of the product of example 8 step A in 9 ml of acetic acid was added dropwise at 60° C. 1.24 g nitric acid (65%; 12.78 mmol). The mixture was stirred at 90° C. for 20 hours. The reaction mixture was cooled to 0° C., filtered and the filter cake was washed with cold water. The solid was dried to give 2.2 g (75%) of the desired product as light yellow crystals.

MS (ESI): 229.0 ([MH]$^+$).

C] Preparation of 4,6-dichloro-5-nitro-nicotinic acid ethyl ester 2.0 g (8.77 mmol) of the product of example 8 step B in 8.0 ml (86 mmol) phosphorus oxychloride were stirred at 80° C. for 74 hours. About half of the phosphorus oxychloride was then removed in vacuo and the remaining mixture was poured onto ice. The mixture was extracted with 3×30 ml of ethyl acetate. The combined organic phases were washed with 30 ml of aqueous sodium carbonate (10%), 2×30 ml water and 30 ml of brine, dried over Na$_2$SO$_4$ and evaporated in vacuo to give the crude product as a brown oil which was purified by column chromatography on silica gel (ethyl acetate/hexane 1:20) to give 1.67 g (72%) of the desired product as light yellow solid.

$^1$H-NMR (DMSO-d$_6$): 9.08 (s, 1H); 4.40 (q, 2H); 1.35 (t, 3H).

D] Preparation of 3-(tert-butyl-dimethyl-silanyloxy)-propylamine

A solution of 7.4 g (98 mmol) 3-aminopropanol in 10 ml THF was added at room temperature to a suspension of 4.12 sodium hydride (60%; 103.2 mmol) in 140 ml THF. The mixture was stirred for 1 hour and then 16.28 g (108 mmol) tert-butyl-dimethylsilylchloride was added and vigorous stirring was continued for 1 hour. The mixture was diluted with 300 ml diethylether and washed successively with 100 ml of aqueous K$_2$CO$_3$ (10%), 100 ml of water and 100 ml of brine, dried over MgSO$_4$ and evaporated to give 17 g of light yellow crude product. This product was dissolved in ethyl acetate/hexane 1/10 and filtered through a pad of silica gel. The filtrate was concentrated in vacuo to give 13 g (70%) of the desired product as a colorless oil.

$^1$H-NMR (CDCl$_3$): 3.67 (t, 2H); 2.78 (t, 2H); 1.83 (s, br, 2H); 1.64 (m, 2H); 0.87 (s, 9H); 0.33 (s, 6H).

E] Preparation of 4-[3-(tert-butyl-dimethyl-silanyloxy)-propylamino]-6-chloro-5-nitro-nicotinic acid ethyl ester A solution of 6.0 g (22.6 mmol) of the product of example 8 step C and 2.3 g (22.6 mmol) triethylamine in 75 ml of ethanol was heated to reflux. 4.0 g (22.6 mmol) of the product of example 8 step D was added to this solution and the mixture was stirred at reflux for an additional hour. The solvent was removed under reduced pressure and the resulting residue was purified by column chromatography on silica gel (hexane/ethyl acetate 80:1) to afford 9 g (95%) of the desired product as yellow oil.

$^1$H-NMR (DMSO-d$_6$): 8.96 (t, 1H); 8.70 (s, 1H); 4.36 (q, 2H); 3.70 (t, 2H); 3.22 (td, 2H); 1.84 (m, 2H); 1.39 (t, 3H); 0.88 (s, 9H); 0.02 (s, 6H).

F] Preparation of 5-amino-4-[3-(tert-butyl-dimethyl-silanyloxy)-propylamino]-6-chloro-nicotinic acid ethyl ester 8.5 g (26.5 mmol) of the product of example 8 step E were dissolved in 100 ml of ethanol and 2.5 g of Raney-nickel were added. The reaction mixture was stirred for 16 hours under an atmosphere of hydrogen gas (1 atm) at room temperature. The catalyst was removed by filtration through a pad of silica gel and the filtrate was concentrated under reduced pressure. The crude product was purified by column chromatography on silica gel (hexane/ethyl acetate 20:1) to afford 5.6 g (58%) of the desired product as brown oil.

MS (ESI): 388.1; 390.1 ([MH]$^±$).

G] Preparation of 1-[3-(tert-butyl-dimethyl-silanyloxy)-propyl]-4-chloro-1H-imidazo[4,5-c]pyridine-7-carboxylic acid ethyl ester 5.6 g (15.5 mmol) of the product of example 8 step F were dissolved in 45 ml triethylorthoformate and the mixture was heated to reflux during 44 hours. The mixture was concentrated under reduced pressure and another 45 ml triethylorthoformate were added and the mixture was heated to reflux for additional 24 hours. The mixture was concentrated under reduced pressure and the residue was purified by column chromatography on silica gel eluting with hexane/ethyl acetate (20/1→5/1) to afford 2.7 g (40%; purity ~62%) of the desired compound as light yellow solid.

$^1$H-NMR (CDCl$_3$): 8.27 (t, 1H); 7.90 (s, 1H); 4.25 (q, 2H); 3.60 (t, 2H); 3.40 (td, 2H); 1.65 (m, 2H); 1.30 (t, 3H); 0.80 (s, 9H); 0.01 (s, 6H).

H] Preparation of 4-amino-1-[3-(tert-butyl-dimethyl-silanyloxy)-propyl]-1H-imidazo[4,5-c]pyridine-7-carboxylic acid ethyl ester Approximately 20 g of ammonia gas was dissolve in 40 ml of ethanol in a 100 ml autoclave and 2.7 g (6.28 mmol; purity ~62%) of the product of example 8 step G were added. The mixture was stirred at 100° C. for 20 hours. The reaction was cooled down and the solvent was evaporated under reduced pressure. The residue was purified by column chromatography on silica gel (DCM/MeOH 100:1 then 50:1) to afford 1.5 g (83%) of a dark brown solid.

I] Preparation of 4-amino-1-[3-hydroxy-propyl]-1H-imidazo[4,5-c]pyridine-7-carboxylic acid ethyl ester 1.5 g (3.4 mmol) of the product of example 8 step H was dissolved in 30 ml dry THF and 1.17 g (~4.5 mmol) tetrabutylammonium fluoride .$H_2O$ was added. The mixture was stirred at room temperature for 1 hour. The solvent was removed under reduced pressure and the residue was purified by column chromatography on silica gel (ethyl acetate, then ethyl acetate/MeOH 50:1 then ethyl acetate/MeOH 20:1) to give 750 mg (69%) of the desired product as a white solid.

$^1$H-NMR (DMSO-$d_6$): 8.31 (s, 1H); 8.08 (s, 1H); 7.00 (s, 2H); 4.59 (t, 2H); 4.26 (q, 2H); 3.22 (t, 2H); 1.72 (m, 2H); 1.29 (t, 3H).

K] Preparation of 4-amino-1-[3-chloro-propyl]-1H-imidazo[4,5-c]pyridine-7-carboxylic acid ethyl ester A suspension of 750 mg (2.36 mmol) of the product of example 8 step I in 22 ml thionyl chloride was stirred at 50° C. for 0.5 hours. 0.275 ml of triethylamine were added and stiffing was continued for 11 hours at 50° C. After completion of the reaction 30 ml of diethyl ether was added to the cooled reaction mixture leading to the formation of a precipitate. The solid was isolated by filtration to give 640 mg (91%) of the desired product as a light yellow powder.

MS (ESI): 283.0 ([MH]$^+$).

$^1$H-NMR (DMSO-$d_6$): 9.00 (s, br, 2H); 8.52 (s, 1H); 8.30 (s, 1H); 4.68 (t, 2H); 4.35 (q, 2H); 3.40 (t, 2H); 2.15 (m, 2H); 1.32 (t, 3H).

L] Preparation of 4-amino-1-[3-chloro-propyl]-1H-imidazo[4,5-c]pyridine-7-carboxylic acid To a mixture of 100 mg (0.35 mmol) of the product of example 8 step K and 0.7 ml of a 2M aqueous solution of LiOH were added 2 ml of THF and 4 ml of MeOH. The mixture was stirred over night at room temperature and then additional 0.7 ml of a 2M aqueous solution of LiOH were added and the mixture was stirred at 45° C. over night. The pH of the mixture was adjusted to pH=7 with 2N aqueous HCl and the solvent was evaporated under reduced pressure. The residue was purified by preparative HPLC (Column: Purospher STAR RP18e, 5 µm, 125×25 mm flow: 25 mL/min; detection: 254 nm; mobile phase A: water+0.1% formic acid; mobile phase B: acetonitrile; gradient: linear form 20% to 60% acetonitirile in 10 min) to give 30 mg (33%) of the desired product as white solid.

M] Preparation of 4-amino-1-[3-chloro-propyl]-1H-imidazo[4,5-c]pyridine-7-carboxylic acid pyridin-4-yl amide A suspension of 60 mg (0.24 mmol) of the product of example 8 step L, 108 mg (0.28 mmol) HATU, 72 mg (0.77 mmol) 4-amino-pyridine and 0.048 ml (0.28 mmol) DIPEA in 4.5 ml DMF was stirred for 3 hours at 30° C. The reaction mixture became clear. Additional 90 mg (0.24 mmol) HATU, 22 mg (0.24 mmol) 4-amino-pyridine and 0.040 ml (0.24 mmol) DIPEA were added to reaction mixture and stirring was continued for another 21 hours. The mixture was concentrated and the crude product was purified by preparative HPLC to give the desired product (containing some formiate) as a white solid. MS (ESI): 331.1; 333.1 ([MH]$^+$).

$^1$H-NMR (DMSO-$d_6$): 10.76 (s, 1H); 8.44 (d, 2H); 8.15 (s, 1H); 8.13 (s, 1H); 7.21 (d, 2H); 6.93 (s, 2H); 4.51 (t, 2H); 3.42 (t, 2H); 2.03 (m, 2H).

N] Preparation of Compound of Formula I where R1 is [3-[4-Amino-7-(pyridin-4-yl-amino-carbonyl)-imidazo[4,5-c]pyridin-1-yl]-propyl]thio, R2 and R3 taken together form a C=O Group and R4 is Methyl. (I-8)

The title compound I-8 was prepared starting from 4-amino-1-[3-chloro-propyl]-1H-imidazo[4,5-c]pyridine-7-carboxylic acid pyridin-4-yl amide (product of example 8 step M) and IX-1 following the procedures described in example 1 steps O-P. The product I-8 was purified by HPLC (System Ap)

$^1$H-NMR (CDCl$_3$): (diagnostic signals only) 8.97 (s, br, 1H); 8.56 (d, 2H); 8.27 (s, 1H); 8.15 (s, 1H); 7.72 (d, br, 2H); 5.82 (s, br, 2H); 5.40 (dd, 1H); 4.91 (d, 1H); 4.60-4.77 (m, 2H); 4.51 (d, 1H); 4.18 (s, 1H); 3.98-4.05 (m, 1H); 3.79 (d, 1H); 3.69 (d, 1H); 3.5-3.6 (m, 1H); 3.35 (s, 3H); 3.08 (s, 3H); 1.42 (s, 3H); 1.37 (s, 3H); 1.15 (d, 3H); 1.08 (d, 3H); 1.01 (d, 3H); 0.85 (t, 3H).

Example 9

Preparation of I-9, compound of formula I where R1 is [3-[4-amino-7-([methoxycarbonylmethyl]-amino-carbonyl)-imidazo[4,5-c]pyridin-1-yl]-propyl]thio, R2 and R3 taken together form a C=O Group and R4 is Methyl A] Preparation of {[4-amino-1-(3-chloro-propyl)-1H-imidazo[4,5-c]pyridine-7-carbonyl]-amino}-acetic acid methyl ester A mixture of 60 mg (0.24 mmol) of the product of example 8 step L, 54 mg (0.28 mmol) EDC, 38 mg (0.28 mmol) HOBt and 89 mg (0.71 mmol) glycine methyl ester HCl salt in 6 ml DMF was stirred for 2 hours at room temperature. The mixture was concentrated and the crude product was purified by preparative HPLC to give 72 mg of the desired product as a white solid.

$^1$H-NMR (DMSO-$d_6$): 9.32 (m, 1H); 8.66 (s, br, 2H); 8.47 (s, 1H); 7.89 (s, 1H); 4.52 (t, 2H); 4.04 (d, 2H); 3.67 (s, 3H); 3.52 (t, 2H); 2.11 (m, 2H).

B] Preparation of Compound of Formula I where R1 is [3-[4-amino-7-([methoxycarbonylmethyl]-amino-carbonyl)-imidazo[4,5-c]pyridin-1-yl]-propyl]thio, R2 and R3 taken together form a C=O Group and R4 is Methyl (I-9)

The title compound I-9 was prepared starting from {[4-amino-1-(3-chloro-propyl)-1H-imidazo[4,5-c]pyridine-7-carbonyl]-amino}-acetic acid methyl ester (product of example 9 step A) and IX-1 following the procedures described in example 1 steps O-P. The product I-8 was purified by HPLC (System Ap) to give the desired product as a white solid.

MS: accurate mass (ESI): 1093.5698 Da.

Example 10

Preparation of I-10, Compound of Formula I where R1 is [2-[4-amino-7-(pyridin-4-yl-amino-carbonyl)-imidazo[4,5-c]pyridin-1-yl]-ethyl]thio, R2 and R3 taken together form a C=O Group and R4 is Methyl

A] Preparation of 4-[2-(tert-butyl-dimethyl-silanyloxy)-ethylamino]-6-chloro-5-nitro-nicotinic acid ethyl ester A solution of 362 mg (1.37 mmol) of the product of example 8 step C and 138 mg (1.37 mmol) triethylamine in 4 ml of ethanol was heated to reflux. 240 mg (1.37 mmol) of 2-(tert-butyl-dimethyl-silanyloxy)-ethylamine was added dropwise to this solution and the mixture was stirred at reflux for an additional hour. The solvent was removed under reduced pressure and the resulting residue was purified by column chromatography on silica gel (hexane/ethyl acetate 80:1) to afford 430 mg (79%) of the desired product as yellow oil.

$^1$H-NMR (DMSO-$d_6$): 9.05 (m, 1H); 8.66 (s, 1H); 4.33 (q, 2H); 3.75 (t, 2H); 3.11 (t, 2H); 1.32 (t, 3H); 0.84 (s, 9H); 0.04 (s, 6H).

B] Preparation of 4-amino-1-[2-chloro-ethyl]-1H-imidazo[4,5-c]pyridine-7-carboxylic acid ethyl ester 4-amino-1-[2-chloro-ethyl]-1H-imidazo[4,5-c]pyridine-7-carboxylic acid ethyl ester was prepared starting from the product of example 10 step A following the procedures described in example 8 steps F to K. The desired product was isolated as light yellow powder.

$^1$H-NMR (DMSO-$d_6$): 9.00 (s, br, 2H); 8.53 (s, 1H); 8.31 (s, 1H); 4.96 (t, 2H); 4.33 (q, 2H); 4.00 (t, 2H); 1.32 (t, 3H).

C] Preparation of 4-amino-1-[2-chloro-ethyl]-1H-imidazo[4,5-c]pyridine-7-carboxylic acid To a mixture of 50 mg (0.19 mmol) of 4-amino-1-[2-chloro-ethyl]-1H-imidazo[4,5-c]pyridine-7-carboxylic acid ethyl ester (example 10 step B) and 1.1 ml of a 2M aqueous solution of NaOH were added 0.3 ml of THF and 0.8 ml of MeOH. The mixture was stirred for 2.5 hours at room temperature. MeOH and THF were evaporated under reduced pressure and the pH of the remaining mixture was adjusted to pH=2 with 2N aqueous HCl. The product precipitated and was isolated by filtration. Toluene was added to the product and the solvent was evaporated. This process was repeated three times. Finally 24 mg (53%) of the desired product were isolated as a light grey solid.

MS (ESI): 241.0 ([MH]$^+$).

$^1$H-NMR (DMSO-$d_6$): 8.35 (s, 1H); 8.14 (s, 1H); 7.06 (s, br, 2H); 4.93 (m, 2H); 3.89 (m, 1H).

D] Preparation of 4-amino-1-[2-chloro-ethyl]-1H-imidazo[4,5-c]pyridine-7-carboxylic acid pyridin-4-yl amide A mixture of 48 mg (0.20 mmol) of the product of example 10 step C, 114 mg (0.30 mmol) HATU, 61 mg (0.65 mmol) 4-amino-pyridine and 0.051 ml (0.30 mmol) DIPEA in 15 ml DMF was stirred overnight at 30° C. The product was directly purified by preparative HPLC to give 47 mg (74%) of the desired product as a white solid.

$^1$H-NMR (DMSO-$d_6$): 10.79 (s, 1H); 8.43 (d, 2H); 8.29 (s, 1H); 8.17 (s, 1H); 7.69 (d, 2H); 6.94 (s, 2H); 4.77 (t, 2H); 3.86 (t, 2H).

E] Preparation of Compound of Formula I where R1 is [2-[4-amino-7-(pyridin-4-yl-amino-carbonyl)-imidazo[4,5-c]pyridin-1-yl]-ethyl]thio, R2 and R3 taken together form a C=O Group and R4 is Methyl (I-10)

The title compound I-10 was prepared starting from 4-amino-1-[2-chloro-ethyl]-1H-imidazo[4,5-c]pyridine-7-carboxylic acid pyridin-4-yl amide (example 10 step D) and IX-4 following the procedure described in example 4 step D. This product was purified by preparative HPLC (system Cp) to give a white solid.

MS: accurate mass (ESI): 1084.5637 Da.

Example 11

Preparation of I-11, compound of formula I where R1 is [2-[4-amino-7-(3,5-dichloro-pyridin-4-yl-amino-carbonyl)-imidazo[4,5-c]pyridin-1-yl]-ethyl]thio, R2 and R3 taken together form a C=O Group and R4 is Methyl

A] Preparation of Compound of Formula I where R1 is [2-[4-amino-7-ethoxycarbonyl-imidazo[4,5-c]pyridin-1-yl]-ethyl]thio, R2 and R3 taken together form a C=O Group and R4 is Methyl To a solution of 1.6 g (1.9 mmol) of the product of example 4 step C (IX-4) and 0.5 ml water in 40 ml DMF were added 765 mg (3.8 mmol) tributylphosphine and the mixture was stirred at room temperature for 3 hours. 400 mg (1.39 mmol) of the product of example 10 step B and 290 mg (1.9 mmol) of DBU were added and the mixture was stirred for 20 hours at 20° C. Then 60 ml of water were added to the reaction and the mixture was extracted with 3×80 ml of ethyl acetate. The combined organic layers were washed with water, dried over Na$_2$SO$_4$ and the solvent was evaporated in vacuo. The crude product was purified by column chromatography on silica gel (DCM/MeOH 40/1, 20/1, 10/1) to give 895 mg (46%) of the desired product as light yellow powder.

MS (ESI): 518.8 ([M+2H]$^{++}$/2)

B] Preparation of Compound of Formula I where R1 is [2-[4-amino-7-carboxyl-imidazo[4,5-c]pyridin-1-yl]-ethyl]thio, R2 and R3 taken together form a C=O Group and R4 is Methyl A mixture of 300 mg (0.3 mmol) of the product of example 11 step A, 3 ml of aqueous LiOH (2N), 8 ml of THF and 6 ml of MeOH was stirred at 18° C. for 20 hours. The reaction mixture was concentrated under reduced pressure and the residue was extracted with 3×50 ml DCM. The combined organic layers were washed with brine, dried over Na$_2$SO$_4$ and the solvent was evaporated in vacuo to give 0.172 g of the crude product. The crude product was purified by preparative HPLC (Column: Purospher Star RP-18e, 5 µm, 125×25 mm flow: 25 mL/min; detection: 254 nm; mobile phase A: water+ 0.1% formic acid; mobile phase B: acetonitrile; gradient: linear from 10% to 40% acetonitrile in 8 min; then 100% acetonitrile) to give a white solid.

MS (ESI): 504.8 ([M+2H]$^{++}$/2)

Ret. Time (system Ba): 12.9 min.

C] Preparation of Compound of Formula I where R1 is [2-[4-amino-7-(3,5-dichloro-pyridin-4-yl-amino-carbonyl)-imidazo[4,5-c]pyridin-1-yl]ethyl]thio, R2 and R3 taken together form a C=O Group and R4 is Methyl (I-11)

153 mg (4.46 mmol) of NaH (60% in oil) were suspended in 1 ml of DMF and a solution of 873 mg (5.3 mmol) 4-amino-3,5-dichloropyridine in 2 ml DMF were added. The suspension was stirred at 25° C. for 3 hours. In parallel, a solution of 260 mg (0.26 mmol) of the product of example 11, step B, 153 mg (0.8 mmol) EDC and 78 mg (0.58 mmol) HOBt in 5 ml DMF was stirred for 1 hour at 25° C. This solution was then added at −5 to 0° C. to the solution of 4-amino-3,5-dichloro-pyridine prepared above. The mixture was stirred at this temperature for 10 minutes and the reaction was quenched with 1 ml of water and the pH of the mixture was adjusted to pH 7-8 with aqueous HCl 2N. The mixture was concentrated and the residue was purified by preparative HPLC (Column: Purospher Star RP-18e, 5 µm, 125×25 mm flow: 25 mL/min; detection: 254 nm; mobile phase A: water+0.01% formic acid; mobile phase B: acetonitrile; gradient: linear from 20% to 60% acetonitrile in 10 min; 5 min with 60% acetonitrile) to give 210 mg (70%) of the desired product as a white solid.

$^1$H-1-NMR (DMSO-$d_6$): 10.68 (s, 1H); 8.70 (t, 2H); 8.31 (s, 1H); 8.24 (s, 1H); 6.97 (t, 2H); 5.15 (m, 1H); 4.85 (m, 1H); 4.72 (m, 1H); 4.62 (m, 1H); 4.40 (m, 3H); 4.00 (m, 1H); 3.66 (m, 1H); 3.58 (t, 2H); 2.40 (s, 6H); 1.80 (m, 2H); 1.65 (m, 2H); 1.51 (m, 3H); 1.40 (s, 3H); 1.29 (s, 3H); 1.05-1.20 (m, 16H); 1.00 (d, 3H); 0.93 (d, 3H); 0.73 (t, 3H).

MS: accurate mass (ESI): 1152.4906 Da.

Example 12

Preparation of I-12, Compound of Formula I where R1 is [2-[6-amino-2-[[(3-pyridyl)methyl]amino]-purin-9-yl]ethyl]thio, R2 and R3 taken together form a C=O Group and R4 is Methyl A] Preparation of 9-(2-chloroethyl)-2,6-diamino-purine 10 g (66.6 mmol) 2,6-diaminopurine were suspended under argon in 300 ml DMF and 21.6 g (156.5 mmol) potassium carbonate and 24 ml 1-bromo-2-chloroethane were added. The mixture was stirred for 64 hours at room temperature. The light yellow suspension was filtered and the solids were washed with 30 ml DMF and subsequently triturated with 100 ml water for 30 minutes. The mixture was filtered and the solids were washed with 50 ml water and dried in vacuo to give 10.15 g (72%) of the desired product as a white solid.

$^1$H-NMR (DMSO-$d_6$): 7.72 (s, 1H); 6.67 (s, br, 2H); 5.81 (s, br, 2H); 4.30 (t, 2H); 3.99 (t, 2H).

B] Preparation of 6-amino-9-(2-chloroethyl)-2-[(3-pyridylmethyl)amino]-purine 100 mg (0.47 mmol) of 9-(2-chloroethyl)-2,6-diamino-purine (example 12, step A) were dissolved in 10 ml MeOH and 3 g molecular sieves (4 Å), 0.044 ml (0.47 mmol) 3-pyridinecarboxaldehyde and 0.135 ml (2.35 mmol) acetic acid were added. The mixture was stirred for 2 hours at room temperature. 23.6 mg (0.38 mmol) sodium cyano-borohydride were added and stiffing was continued for 4 hours. Additional 0.044 ml (0.47 mmol) 3-pyridinecarboxaldehyde were added and 72 mg sodium cyano-borohydride were added in three portions over three days at room temperature. The solvent was evaporated and the residue was taken up in 50 ml ethyl acetate. The organic layer was washed with sat. aqueous sodium carbonate and brine, dried over $Na_2SO_4$ and the solvent was evaporated in vacuo to give 0.254 g of the crude product as yellow oil. The crude product was purified by flash chromatography on silica gel (DCM/MeOH 99.5/0.5→80:20) to give 88 mg of the desired product as white solid.

$^1$H-NMR (DMSO-$d_6$): 8.57 (s, 1H); 8.40 (m, 1H); 7.74 (s, br, 1H); 7.73 (s, 1H); 7.30 (m, 1H); 6.99 (m, 1H); 6.75 (s, br, 2H); 4.45 (d, 2H); 4.30 (t, 2H); 3.95 (t, 2H).

C] Preparation of, Compound of Formula I where R1 is [2-[6-amino-2-[[(3-pyridyl)methyl]amino]-purin-9-yl]ethyl]thio, R2 and R3 taken together form a C=O Group and R4 is Methyl (I-12)

The title compound I-12 was prepared starting from 6-amino-9-(2-chloroethyl)-2-[(3-pyridylmethyl)amino]-purine (product of example 12 step B) and IX-1 following the procedures described in example 1 steps O-P. The crude product was purified by HPLC (System Ap) to give the desired product as a white solid.

MS: accurate mass (ESI): 1071.5826 Da.

Example 13

Preparation of I-13, Compound of Formula I where R1 is [2-[6-amino-2-[[(4-pyridyl)methyl]amino]-purin-9-yl]ethyl]thio, R2 and R3 taken together form a C=O Group and R4 is Methyl A] Preparation of 6-amino-9-(2-chloroethyl)-2-[(4-pyridylmethyl)amino]-purine 6-amino-9-(2-chloroethyl)-2-[(4-pyridylmethyl)amino]-purine was prepared from 4-pyridinecarboxaldehyde and 9-(2-chloroethyl)-2,6-diamino-purine according to the procedure described in example 12 step B. The crude product was purified by flash chromatography (DCM/MeOH 99.5/0.5→80:20) to give the desired product as white solid.

$^1$H-NMR (DMSO-$d_6$): 8.44 (d, 2H); 7.73 (s, 1H); 7.31 (d, 2H); 7.01 (t, 1H); 6.75 (s, br, 2H); 4.46 (d, 2H); 4.27 (t, 2H); 3.91 (t, 2H).

B] Preparation of, Compound of Formula I where R1 is [2-[6-amino-2-[[(4-pyridyl)methyl]amino]-purin-9-yl]ethyl]thio, R2 and R3 taken together form a C=O Group and R4 is Methyl (I-13)

The title compound I-12 was prepared starting from 6-amino-9-(2-chloroethyl)-2-[(4-pyridylmethyl)amino]-purine (product of example 13 step A) and IX-1 following the procedures described in example 1 steps O-P. The crude product was purified by HPLC (System Ap) to give the desired product as a white solid.

MS: accurate mass (ESI): 1071.5826 Da.

B. BIOLOGICAL ACTIVITY

The compounds of the invention exhibit substantial inhibitory activity towards human phosphodiesterases (PDEs), in particular towards PDE4. The following assay has been used to determine the inhibitory activity of the compounds.

Assay

PDE4 specifically hydrolyzes cAMP and releases the product AMP. The potency of PDE inhibition by said agents was determined in an in vitro enzymatic assay. The assay is commercially available (IMAP™ FP assay Molecular Devices Corp.) and was optimized for the use of human PDE4. Fluorescently labeled cAMP was hydrolyzed by PDE4 and in a second step, binding of labeled product to a large binding partner allowed product detection by fluorescence polarization (FP) measurements.

PDE4 was partially purified from undifferentiated human monocytic cells (U-937) according to Thorpy et al. 1992 (*J. Pharmacol. Exp. Ther.* 263: 1195). Final preparations were specific for cAMP and did not hydrolyze cGMP above the detection limit of the assay. In addition, PDE4 preparations were validated by inhibition studies with PDE4-specific and unspecific PDE inhibitors.

Stock solutions of test compounds were made in DMSO and diluted in assay buffer (10 mM Tris-HCl, 10 mM $MgCl_2$, 0.1% BSA 0.05% $NaN_3$, pH 7.2) to the desired concentrations. The solutions used in the assay contained test compound in assay buffer with 2% DMSO.

10 µl of substrate (at a concentration recommended by the manufacturer) were mixed with 5 µl of appropriately diluted PDE and 5 µl of test compound solution. 5 µl of reaction buffer with 2% DMSO were used for control reactions. The final concentration of DMSO in the assay was 0.5%, which did not significantly alter the PDE activity. After incubation for 90 minutes at room temperature, 60 µl of binding reagent were added as specified by the manufacturer. Binding was allowed to proceed for 30 minutes and fluorescence polarization was measured. Dose dependence of PDE inhibition was measured by assaying dilution series of test compounds in duplicates. $IC_{50}$ values were determined from the measured activities by curve fitting.

Results

| Example | $IC_{50}$ (PDE4) [µM] |
|---|---|
| 1 | 13.4 |
| 2 | 3.9 |
| 3 | 3.4 |
| 4 | 0.28 |
| 5 | 0.85 |
| 6 | 0.37 |
| 7 | 7.6 |
| 8 | 4.7 |
| 9 | 24.2 |
| 10 | 1.0 |
| 11 | 0.008 |
| 12 | 3.8 |
| 13 | 2.6 |

The PDE4-inhibiting activity found for the compounds of this invention as shown in the examples is particularly surprising because the basic macrolide of the exemplified compounds which has the following formula:

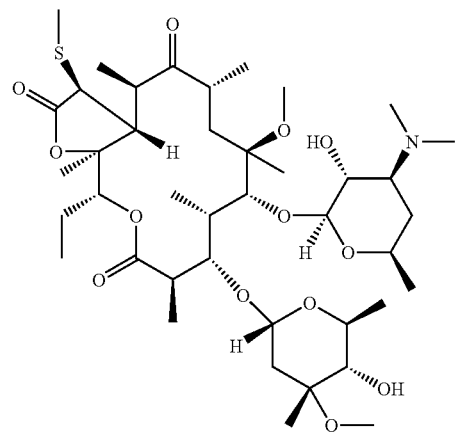

does not show any PDE4-inhibiting activity up to a concentration of 50 µM in the assay used in the examples and, even if the substituent linked to said basic macrolide in one of the compounds of the present invention when used in free form shows a certain PDE4-inhibiting activity in said assay like, for example, the following compound

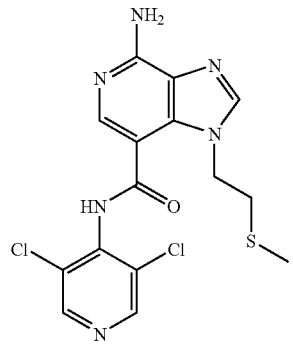

which has a value for $IC_{50}$(PDE4) of 3.6 µM, the PDE4-inhibiting activity of the respective compound according to the present invention wherein the very same compounds are linked together to form a molecule of formula (I), generally show a PDE4-inhibiting activity which is strongly improved over the corresponding activity of its partial components as well as over the activity to be reasonably expected for a mixture of said partial components. In the present case, for example, an $IC_{50}$(PDE4) of 0.008 µM is found for the compound of Example 11 having the formula:

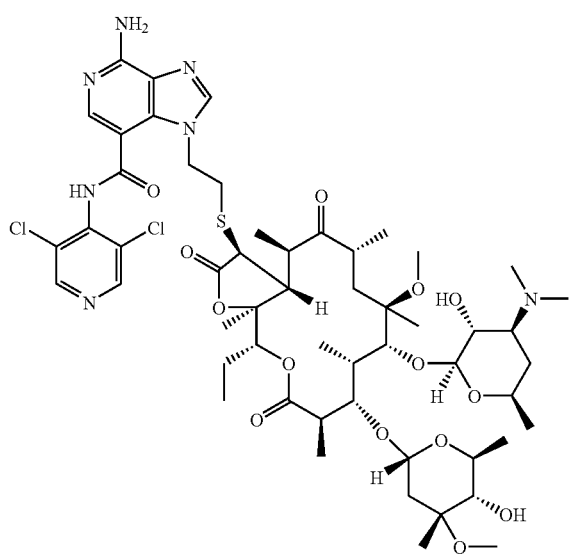

which is only about one five hundredth of the $IC_{50}(PDE4)$ for the macrolide substituent in free form.

The invention claimed is:

1. Macrolide compound of formula I:

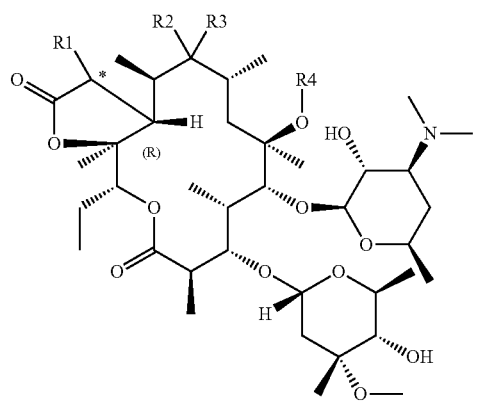

wherein
R1 is a residue —Y—X-Q;
Y is S;
X is a linear group consisting of hydrogen atoms and from 2 to 5 other additional atoms individually selected from the group consisting of C, N, O and S;
Q is a residue —V-A1-L-A2-W or —NR6R7;
V is a divalent group of formula

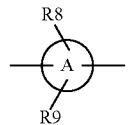

wherein

is a phenylene ring or a x-membered heteroaromatic ring containing from 2 to (x-1) carbon atoms with x being 5 or 6, and from 1 to 3 hetero nitrogen atoms, R8 and R9 are independently selected from the group consisting of hydrogen, $C_1$-$C_4$alkyl, $C_1$-$C_4$alko $C_3$-$C_7$cycloalkyloxy, $C_3$-$C_7$cycloalkyl-$C_1$-$C_4$alkoxy, halogen, halogen-sub-stituted $C_1$-$C_4$alkyl groups, cyano, nitro, amino, $C_1$-$C_4$alkylamino, di($C_1$-C4)alkylamino, $C_1$-$C_4$alkylthio, mercapto, hydroxy, carbamoyl carboxy, and when both substituents R8 and R9 are located at adjacent carbon atoms of the ring

these two substituents can be taken together with said adjacent carbon atoms to form a 5- or 6-membered aromatic or a x-membered heteroaromatic ring containing from 2 to (x-1) carbon atoms with x being 5 or 6, and from 1 to 3 hetero nitrogen atoms, wherein V can have from one to four substituents of the kind as defined for R8 and R9 and the free valences can be located either on one or on both rings of the group V;

W is a group of formula

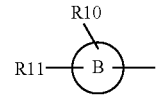

wherein

is a heteroaromatic ring containing from 2 to (x-1) carbon atoms with x being 5 or 6, and from 1 to 3 hetero nitrogen atoms, R10 and R11 are independently selected from the group consisting of hydrogen $C_1$-$C_4$alkyl, $C_1$-$C_4$alkoxy, $C_3$-$C_7$cycloalkyoxy, $C_3$-$C_7$cycloalkyl-$C_1$-$C_4$alkoxy, halogen, halogen-substituted $C_1$-$C_4$alkyl groups, cyano, nitro, amino, $C_1$-$C_4$alkylamino, di($C_1$-C4)alkylamino, $C_1$-$C_4$alkylthio, mercapto, hydroxy, carbamoyl and carboxyl, A1, A2 are independently of each other either absent or a $C_1$-$C_4$alkylene group;
L is —NH—, —(CO)NH— or —NH(CO)—;
R2, R3 taken together with their attached carbon atom form a C=O group;
R4 is hydrogen or methyl;
R6, R7 are independently selected from the group consisting of aryl; aralkyl; heterocyclyl and heterocyclylalkyl; and one of R6 and R7 can also be a group (C=O)W; and
* indicates a chiral centre which is in the (R) or (S) form; except for the compound of formula I, wherein
R1 is

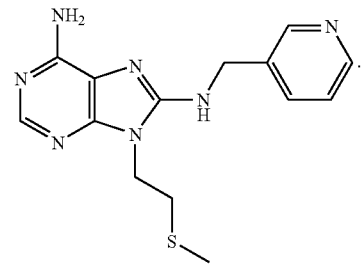

2. The compound of claim 1, wherein
Q is a residue —V-A1-L-A2-W.
3. The compound of claim 1, wherein
Q is —NR6R7.
4. The compound of claim 3, wherein
V is a divalent group selected from the group consisting of

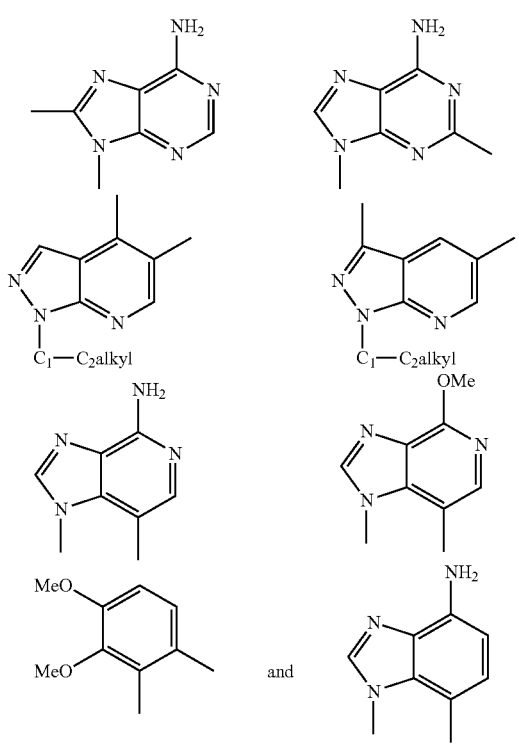
5. The compound of claim 1, wherein
W is a group of one of the formulae
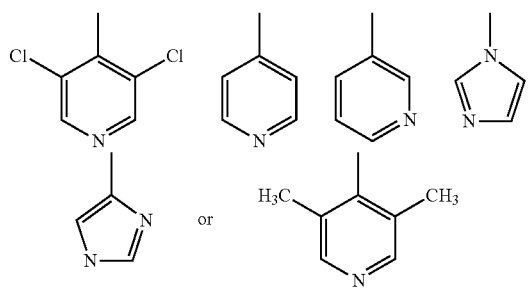
6. The compound of claim 1, wherein
V is a divalent group of formula
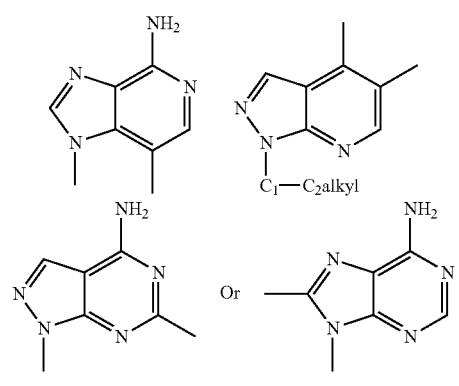
and
W is a group of formula
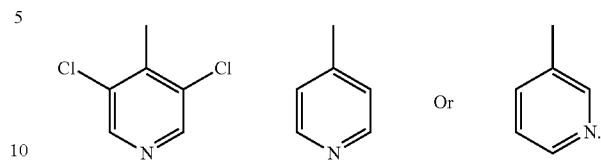
7. The compound of claim 6, wherein
X is —CH$_2$—CH$_2$—NH— which is linked to residue Q via the NH group.
8. The compound of claim 3, wherein
—NR6R7 are a group of one of the following formulae
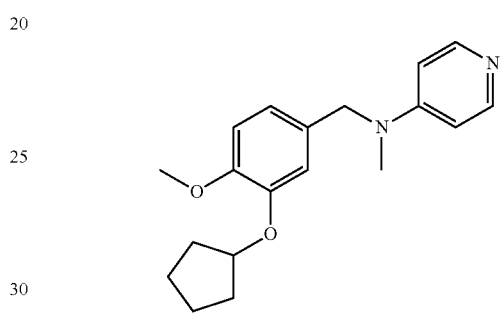
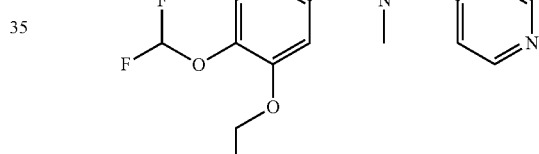
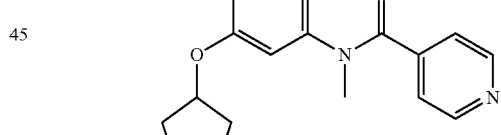
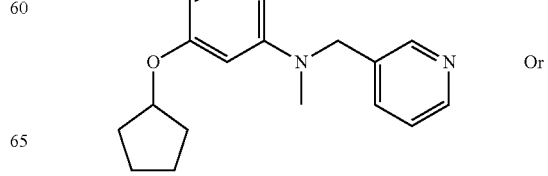

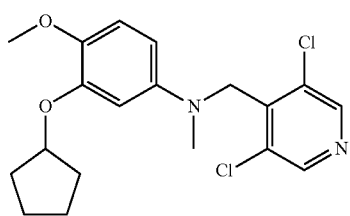
9. The compound of claim 2 having the formula
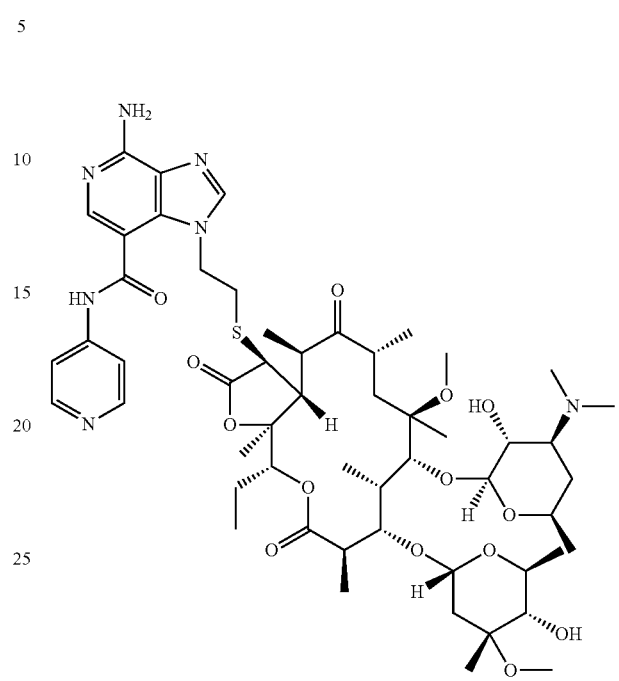
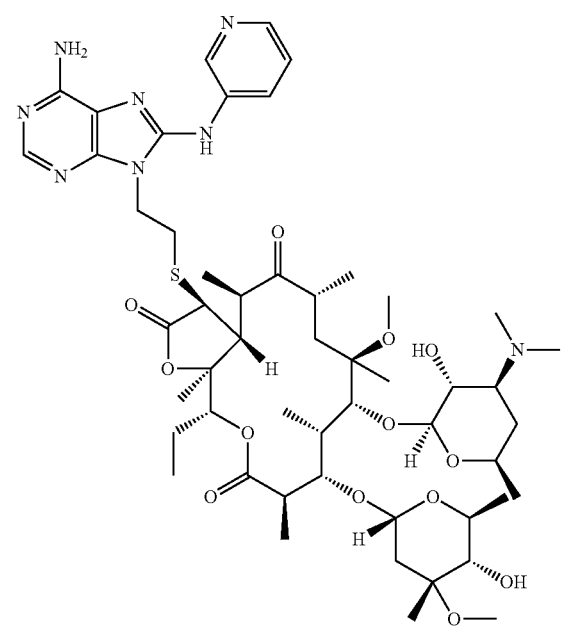
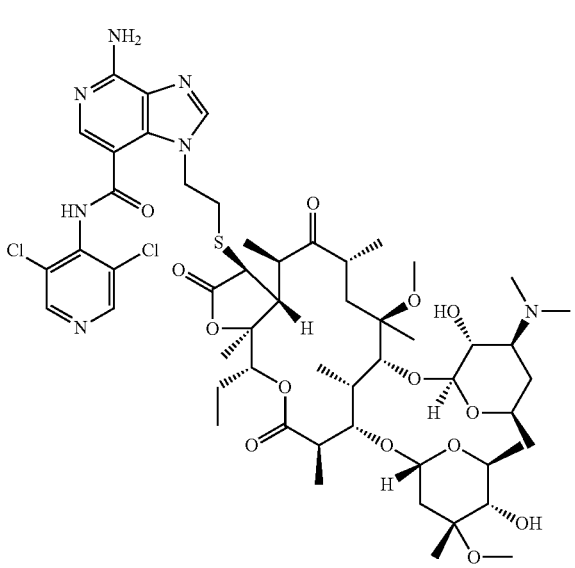
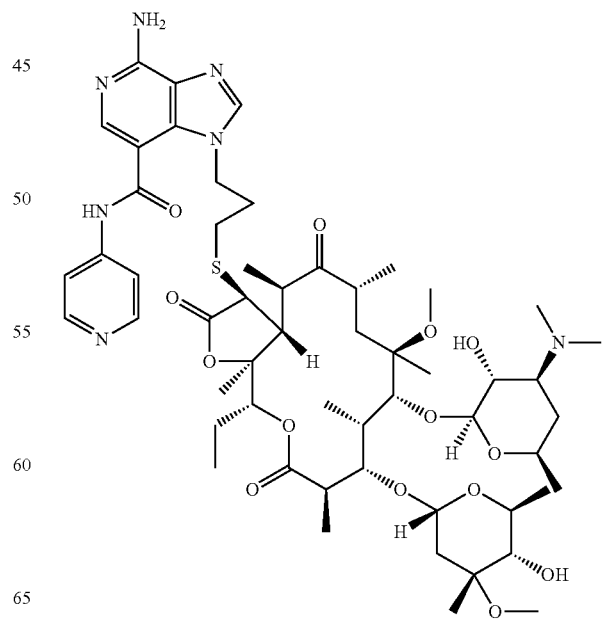

-continued
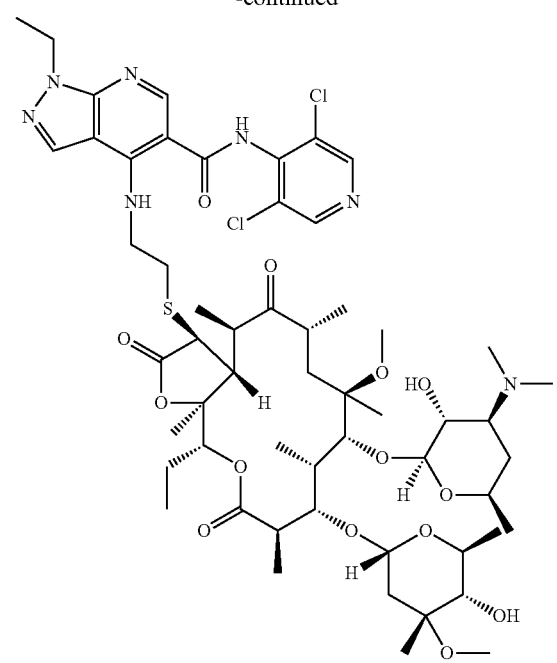
Or
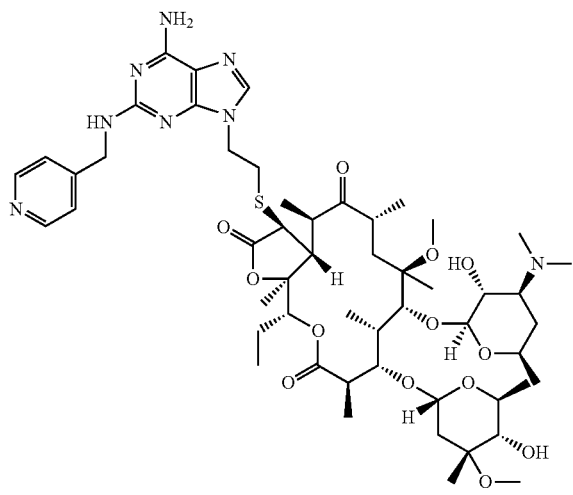
10. The compound of claim 1 having the formula
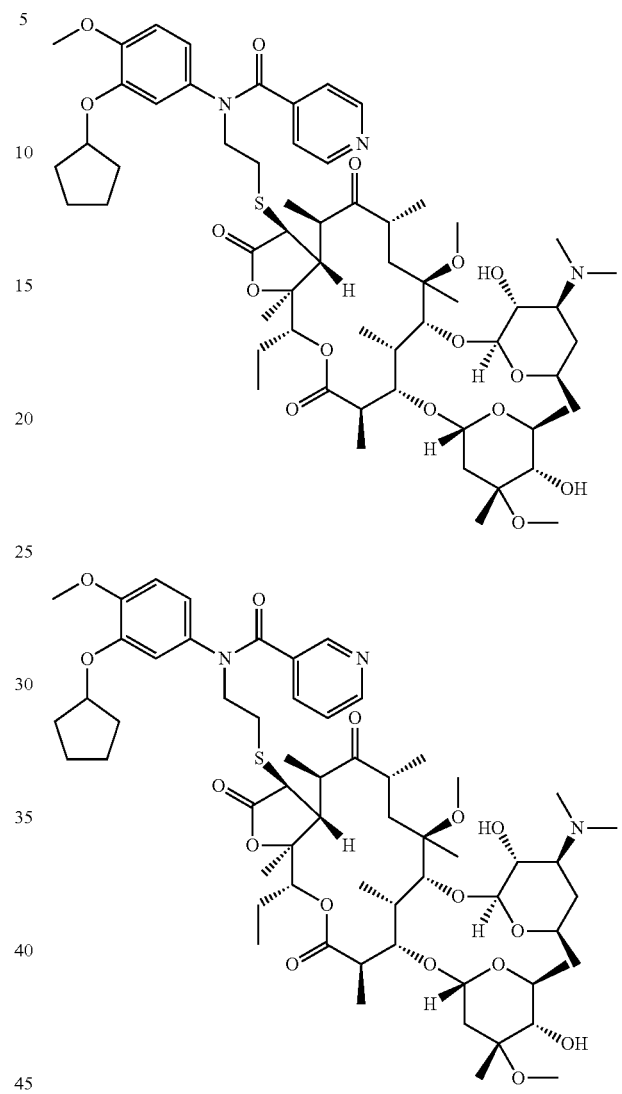
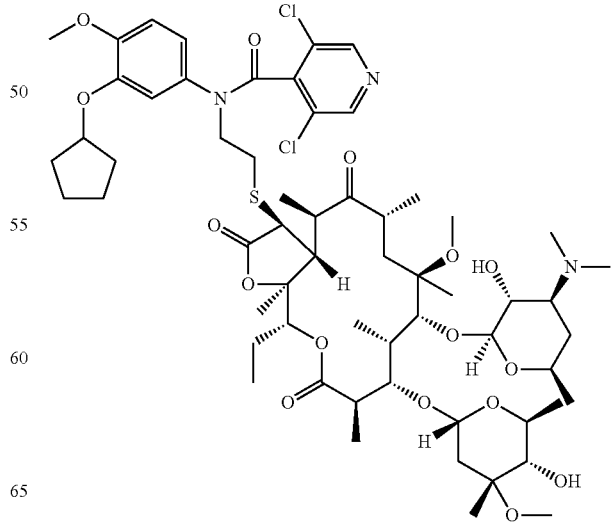

-continued

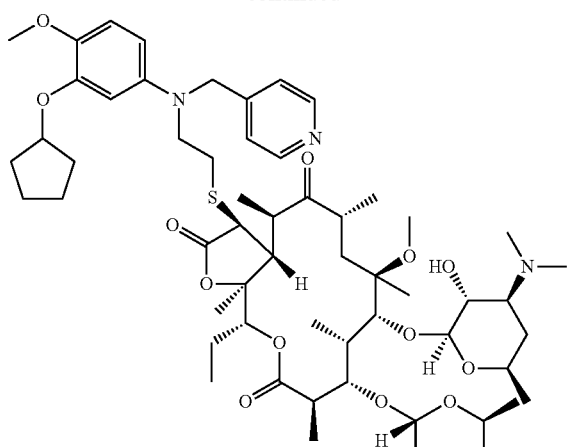

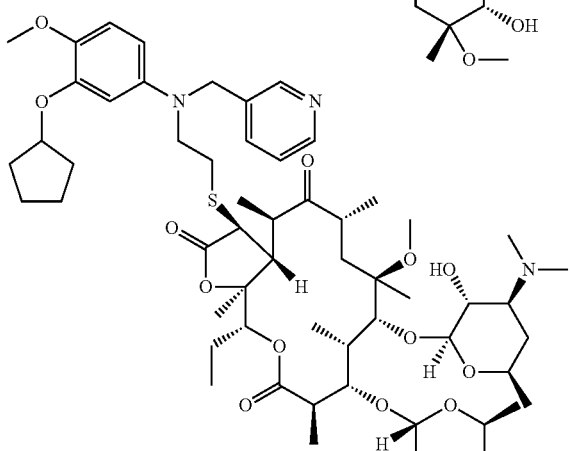

Or

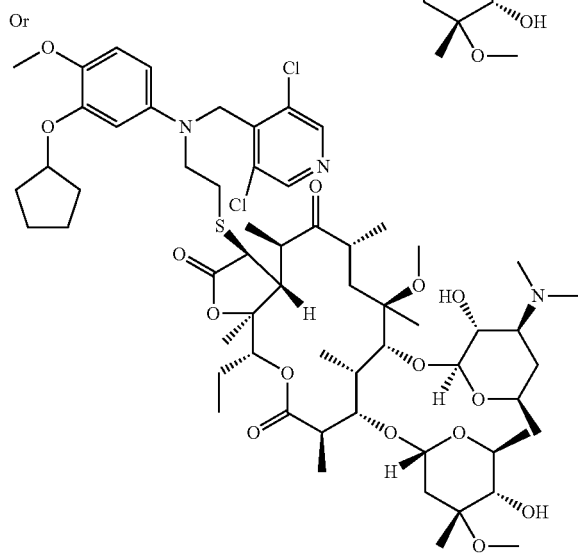

11. The compound of claim 9, wherein

R6 and R7 are independently selected from the group consisting of aryl; aralkyl; heterocyclyl and heterocyclylalkyl wherein "aryl" and "ar" in "aralkyl" mean phenyl which is unsubstituted or substituted with one or two substituents selected from $C_1$-$C_4$alkoxy, $C_3$-$C_7$cycloalkyloxy, $C_3$-$C_7$cycloalkyl-$C_1$-$C_4$alkoxy and halogen, "heterocyclyl" means 3- or 4-pyridyl which is unsubstituted or substituted with one or more halogen atoms, and "alkyl" means $C_1$-$C_6$alkyl.

12. The compound of claim 11, wherein

R6 and R7 are aryl or heterocyclylalkyl.

13. The compound of claim 6 wherein X is —CH$_2$—CH$_2$—.

14. A method for the treatment of a human affected by a disorder or disease which can be ameliorated by inhibition of human phosphodiesterase 4 comprising administering an effective amount of a compound of formula I of claim 1 to a patient in need of said treatment, said amount being sufficient to inhibit human phosphodiesterase 4 in said patient.

15. A method of treating chronic obstructive pulmonary disease (COPD) comprising administering an effective amount of a compound of formula I of claim 1 to a patient in need of said treatment, said amount being sufficient to inhibit chronic obstructive pulmonary disease (COPD).

\* \* \* \* \*